US012636378B2

(12) United States Patent
Brown et al.

(10) Patent No.: US 12,636,378 B2
(45) Date of Patent: May 26, 2026

(54) TARGETED ANTIGEN DELIVERY SYSTEM AND USES THEREOF

(71) Applicant: SRI International, Menlo Park, CA (US)

(72) Inventors: Kathlynn C. Brown, Menlo Park, CA (US); Michael J. McGuire, Menlo Park, CA (US); Indu Venugopal, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 18/246,083

(22) PCT Filed: Sep. 21, 2021

(86) PCT No.: PCT/US2021/051332
§ 371 (c)(1),
(2) Date: Mar. 21, 2023

(87) PCT Pub. No.: WO2022/061297
PCT Pub. Date: Mar. 24, 2022

(65) Prior Publication Data
US 2023/0364261 A1 Nov. 16, 2023

Related U.S. Application Data

(60) Provisional application No. 63/081,178, filed on Sep. 21, 2020.

(51) Int. Cl.
| | |
|---|---|
| *A61K 47/69* | (2017.01) |
| *A61K 39/145* | (2006.01) |
| *A61P 35/00* | (2006.01) |
| *C07K 14/11* | (2006.01) |
| *A61K 38/00* | (2006.01) |

(52) U.S. Cl.
CPC ........ *A61K 47/6911* (2017.08); *A61K 39/145* (2013.01); *A61P 35/00* (2018.01); *C07K 14/11* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 11,738,098 B2 * | 8/2023 | Yang ...................... | A61K 49/14 |
| | | | 530/387.3 |
| 2006/0051746 A1 | 3/2006 | Chisari | |

| | | | |
|---|---|---|---|
| 2013/0164364 A1 * | 6/2013 | Paulson .................. | A61P 29/00 |
| | | | 435/375 |
| 2014/0286982 A1 | 9/2014 | Ben-Yedidia et al. | |
| 2017/0252417 A1 | 9/2017 | Irvine et al. | |
| 2017/0281752 A1 | 10/2017 | Brown et al. | |
| 2019/0315827 A1 | 10/2019 | Roep et al. | |

FOREIGN PATENT DOCUMENTS

| | | |
|---|---|---|
| WO | 2019014190 A1 | 1/2019 |

OTHER PUBLICATIONS

Weidanz et al (J Immunol, 2006, 177: 5088-5097.*
Ota et al (The Journal of Infectious Disease, 2007, 195: 1799-1807.*
PCT International Search Report, mailed Jan. 12, 2022, in connection with International Application No. PCT/US2021/051332, all pages.
PCT Written Opinion, mailed Jan. 12, 2022, in connection with International Application No. PCT/US2021/051332, all pages.
Umlauf et al., "Modular Three-component Delivery System Facilitates HLA Class I Antigen Presentation and CD8(+) T-cell Activation Against Tumors", Molecular Therapy, vol. 23, No. 6, Jun. 2015, pp. 1092-1102.
Umlauf et al: "Identification of a Novel Lysosomal Trafficking Peptide using Phage Display Biopanning Coupled with Endocytic Selection Pressure", Bioconjugate Chemistry, vol. 25, No. 10, Oct. 15, 2014 (Oct. 15, 2014), pp. 1829-1837, XP055387 486, us ISSN: 1043-1802, DOI: 10.1021/bc500326x.

* cited by examiner

*Primary Examiner* — Michail A Belyavskyi
(74) *Attorney, Agent, or Firm* — Dicke, Billig & Czaja, PLLC

(57) ABSTRACT

Disclosed are antigen delivery systems comprising a nanoparticle, wherein the nanoparticle is surface-modified with a cancer-specific cell targeting peptide and comprises an immunogenic HLA class I restricted peptide, wherein the HLA class I restricted peptide is a vaccine-dependent, immunogenic HLA class I restricted peptide; methods of treating a subject having cancer comprising administering said delivery systems; methods of killing cancer cells comprising contacting cancer cells delivery systems, wherein upon entry of the liposome into the cancer cells, the cancer cells present said peptide from said delivery system, wherein the cancer cells generate an immune response said peptide, and wherein the immune response to said peptide targets and kills the cancer cells presenting the vaccine-dependent, peptide; methods of generating a non-cancer secondary immune response that targets cancer cells comprising administering said delivery systems to a subject having cancer cells.

9 Claims, 24 Drawing Sheets

Specification includes a Sequence Listing.

Conductivity:        0.0572 mS/cm
Effective voltage:   4.56 V

Count Rate:          127.0 kcps

Peak 1:              Peak / Area
                     -25.3 mV / 100.0%

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: synthetic construct; targeting sequence

<400> SEQUENCE: 1

Leu Gln Trp Arg Arg Asn Phe Gly Val Trp Ala Arg Tyr Arg Leu
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: synthetic construct; targeting sequence

<400> SEQUENCE: 2

Leu Gln Trp Arg Arg Asp Asp Asn Val His Asn Phe Gly Val Trp Ala
1               5                   10                  15

Arg Tyr Arg Leu
            20

<210> SEQ ID NO 3
<211> LENGTH: 31
<212> TYPE: PRT
<213> ORGANISM: Artificial Sequence
<220> FEATURE:
<223> OTHER INFORMATION: synthetic construct; targeting peptide
<220> FEATURE:
<221> NAME/KEY: misc
<222> LOCATION: (15)..(16)
<223> OTHER INFORMATION: PEG11 linker between L and K
<220> FEATURE:
<221> NAME/KEY: misc
<222> LOCATION: (16)..(17)
<223> OTHER INFORMATION: PEG11 linker between K and L
```

-continued

```
<400> SEQUENCE: 3

Leu Gln Trp Arg Arg Asn Phe Gly Val Trp Ala Arg Tyr Arg Leu Lys
1               5                   10                  15

Leu Arg Tyr Arg Ala Trp Val Gly Phe Asn Arg Arg Trp Gln Leu
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: synthetic construct; targeting peptide
<220> FEATURE:
<221> NAME/KEY: misc
<222> LOCATION: (15)..(16)
<223> OTHER INFORMATION: PEG11 linker between L and K
<220> FEATURE:
<221> NAME/KEY: misc
<222> LOCATION: (16)..(17)
<223> OTHER INFORMATION: PEG11 linker between K and L
<220> FEATURE:
<221> NAME/KEY: misc
<222> LOCATION: (16)..(16)
<223> OTHER INFORMATION: Lys branchpoint can have a tag or reactive
      moiety for conjugation

<400> SEQUENCE: 4

Leu Gln Trp Arg Arg Asn Phe Gly Val Trp Ala Arg Tyr Arg Leu Lys
1               5                   10                  15

Leu Arg Tyr Arg Ala Trp Val Gly Phe Asn Arg Arg Trp Gln Leu
            20                  25                  30

<210> SEQ ID NO 5
<211> LENGTH: 10
<212> TYPE: PRT
<213> ORGANISM: Artificial Sequence
<220> FEATURE:
<223> OTHER INFORMATION: synthetic construct; H250 peptide

<400> SEQUENCE: 5

Ser Met Tyr Arg Val Phe Glu Val Gly Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: synthetic construct; C166 peptide

<400> SEQUENCE: 6

Ser Leu Trp Gly Ser Leu Leu Met Leu
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic construct; H38 peptide

<400> SEQUENCE: 7

Leu Leu Ala Val Ile Phe Val Met Phe Leu
1               5                   10

<210> SEQ ID NO 8
<211> LENGTH: 10
```

```
<212> TYPE: PRT
<213> ORGANISM: Artificial Sequence
<220> FEATURE:
<223> OTHER INFORMATION: synthetic construct; H516 peptide

<400> SEQUENCE: 8

Ile Leu Pro Gly Gln Asp Leu Gln Tyr Val
1               5                   10

<210> SEQ ID NO 9
<211> LENGTH: 9
<212> TYPE: PRT
<213> ORGANISM: Artificial Sequence
<220> FEATURE:
<223> OTHER INFORMATION: synthetic construct; H3L peptide

<400> SEQUENCE: 9

Ser Leu Ser Ala Tyr Ile Ile Arg Val
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic construct; E2L peptide

<400> SEQUENCE: 10

Lys Ile Asp Tyr Tyr Ile Pro Tyr Val
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic construct; Q1L peptide

<400> SEQUENCE: 11

Gly Leu Asn Asp Tyr Leu His Ser Val
1               5

<210> SEQ ID NO 12
<211> LENGTH: 40
<212> TYPE: DNA
<213> ORGANISM: Artificial Sequence
<220> FEATURE:
<223> OTHER INFORMATION: synthetic construct; primer

<400> SEQUENCE: 12
agaggatcca ccggtcgcca ccatggaaga tgccaaaaac                          40

<210> SEQ ID NO 13
<211> LENGTH: 30
<212> TYPE: DNA
<213> ORGANISM: Artificial Sequence
<220> FEATURE:
<223> OTHER INFORMATION: synthetic construct; primer

<400> SEQUENCE: 13
atagctcgag ttagacgttg atcctggcgc                                    30
```

TARGETED ANTIGEN DELIVERY SYSTEM AND USES THEREOF

CROSS-REFERENCE TO RELATED APPLICATIONS

This application is a U.S. National Stage Entry of International Application No. PCT/US21/51332, filed on Sep. 21, 2021, and claims the benefit of U.S. Provisional Patent Application No. 63/081,178, filed on Sep. 21, 2020, each of which is incorporated by reference herein in its entirety.

STATEMENT REGARDING FEDERALLY SPONSORED RESEARCH

This invention was made with government support under W81XWH-16-1-0262 awarded by USA Medical Research Acquisition Activity (USAMRAA), and support under 7R01CA164447 and 5R01CA164447 awarded by The National Institute of Health. The government has certain rights to this invention.

REFERENCE TO SEQUENCE LISTING

The Sequence Listing submitted September 21, 2021 as a text file named "37794_0097P1 Sequence Listing.txt," created on September 21, 2021, and having a size of 3,894 bytes is hereby incorporated by reference pursuant to 37 C.F.R. § 1.52(e)(5).

BACKGROUND

Cell-mediated (CM) immunotherapies for cancer treatment are designed to activate the body's adaptive immune responses against a malignant growth. Generally, the goal of a CM response is to activate a cytotoxic T-cell response against a tumor to eliminate cancer cells. The principle of these treatments is straightforward, yet current work studying the complexity of the tumor micro-environment as well as methods that attempt to directly activate T cells against tumor antigens demonstrate the difficulty associated with generating an immune response against a tumor.

Several CM cancer immunotherapies exist today, including PD-1 inhibitors, injection of live virus or viral particles into tumors, and adoptive T-cell therapies. However, concerns regarding efficacy, safety, and/or cost have limited the use of many of these treatments. To address these concerns, a treatment based on developing a fully synthetic, minimal delivery system that facilitates presentation of human leukocyte antigen (HLA) class I restricted immunogenic peptides specifically on cancer cells without using live virus, viral subunits, or biologically derived material can be used to generate an immune response to the HLA class I peptide.

A liposomal based agent consisting of a neutral, stealth liposome that encapsulates a synthetically manufactured immunogenic HLA class I restricted peptide has been developed. In addition, the liposome has a targeting peptide on the external surface that both specifically accumulates in cancer cells and facilitates presentation of the immunogenic peptide in HLA class I molecules. Disclosed herein are targeting peptides that show better efficacy in the antigen delivery system.

BRIEF SUMMARY

Disclosed is an immunotherapy based on an antigen delivery system to facilitate presentation of non-cancer HLA class 1 restricted immunogenic peptides in cancer cells, resulting in a secondary immune response against the cancer cells.

Disclosed are antigen delivery systems comprising a nanoparticle, wherein the nanoparticle is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1). An example of the disclosed antigen delivery systems, is an antigen delivery system comprising a PEGylated liposome, wherein the PEGylated liposome is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

Disclosed are methods of treating a subject having cancer comprising administering one of the antigen delivery systems disclosed herein to a subject having cancer. For example, disclosed are methods of treating a subject having cancer comprising administering an antigen delivery system comprising a PEGylated liposome, wherein the PEGylated liposome is surface-modified with a cancer-specific cell targeting peptide and comprises an immunogenic human leukocyte antigen (HLA) class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

Disclosed are methods of treating a subject having cancer comprising administering one of the antigen delivery systems disclosed herein to a subject having cancer. For example, disclosed are methods of treating a subject having cancer comprising administering an antigen delivery system comprising a PEGylated liposome, wherein the PEGylated liposome is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

Disclosed are methods of killing cancer cells comprising contacting cancer cells with any of the antigen delivery systems disclosed herein, wherein upon entry of the liposome into the cancer cells, the cancer cells present the vaccine-dependent, immunogenic HLA class I restricted peptide from the antigen delivery system, wherein the cancer cells generate an immune response to the vaccine-dependent, immunogenic HLA class I restricted peptide, and wherein the immune response to the vaccine-dependent, immunogenic HLA class I restricted peptide targets and kills the cancer cells presenting the vaccine-dependent, immunogenic HLA class I restricted peptide.

Disclosed are methods of generating a non-cancer secondary immune response that targets cancer cells comprising administering one of the antigen delivery systems disclosed herein to a subject having cancer cells, wherein, upon entry of the liposome into the cancer cell in the subject, the cancer cell presents the vaccine-dependent, immunogenic HLA class I restricted peptide from the antigen delivery system, wherein the subject generates a non-cancer secondary immune response to the vaccine-dependent, immunogenic HLA class I restricted peptide, wherein the non-cancer secondary immune response targets and kills the cancer cells presenting the vaccine-dependent, immunogenic HLA class I restricted peptide.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
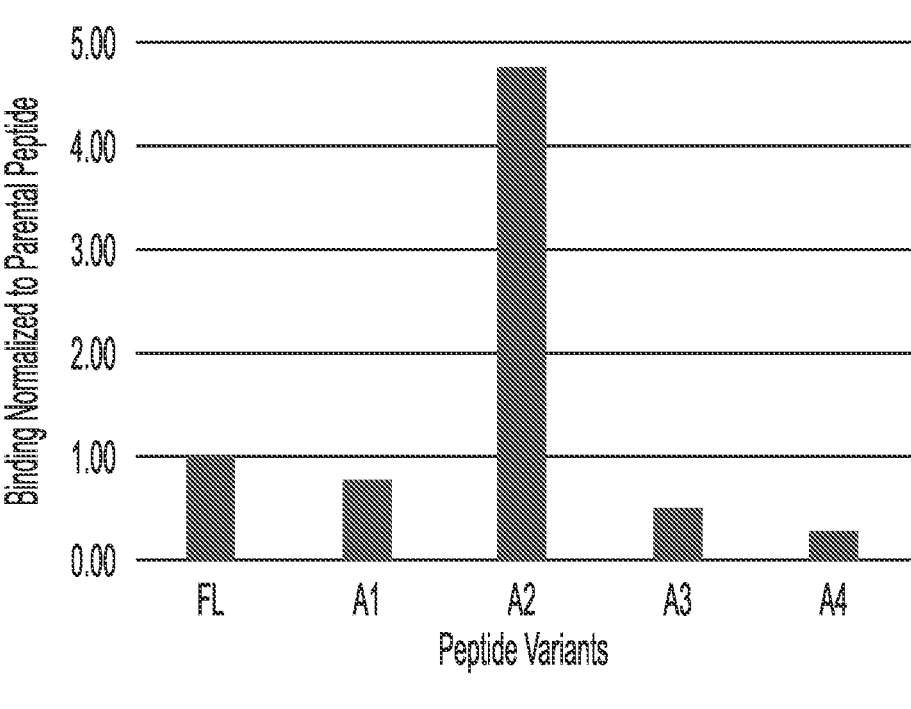
FIG. 1 shows exemplary flow cytometry results showing normalized of alanine variants (A1, A2, A3 and A4) of SRI_MGS5 on H1993 cells.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a targeting peptide" includes a plurality of such targeting peptides, reference to "the liposome" is a reference to one or more liposomes and equivalents thereof known to those skilled in the art, and so forth.

As used herein, the term "subject" or "patient" can be used interchangeably and refer to any organism to which a protein or composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like.

By "treat" is meant to administer an antigen delivery system or composition of the invention to a subject, such as a human or other mammal (for example, an animal model), that has an increased susceptibility for developing cancer or that has cancer, in order to prevent or delay a worsening of the effects of the disease or condition, or to partially or fully reverse the effects of the disease or condition.

By "prevent" is meant to minimize the chance that a subject who has an increased susceptibility for developing cancer actually develops the disease or otherwise develops a cause of symptom thereof.

As used herein, the terms "administering" and "administration" refer to any method of providing a disclosed peptide, composition, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration for a disclosed composition or a disclosed protein so as to treat a subject or induce an immune response. In an aspect, the skilled person can also alter or modify an aspect of an administering step so as to improve efficacy of a disclosed antigen delivery system or a pharmaceutical preparation.

The term "percent (%) identity" can be used interchangeably herein with the term "percent (%) homology" and refers to the level of nucleic acid or amino acid sequence identity when aligned with a wild type sequence using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for anyone of the inventive proteins, as described herein. Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997. Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62matrix. (See, e.g., Altschul, S. F., et al., Nucleic Acids Res.25:3389-3402, 1997.) A preferred alignment of selected sequences in order to determine "% identity" between two or more sequences, is performed using for example, the CLUSTAL-W program in Mac Vector version 13.0.7, operated with default parameters, including an open gap penalty of 10.0, an extended gap penalty of 0.1, and a BLOSUM 30 similarity matrix.

Amino acid alterations such as substitutions, deletions, insertions or any combination thereof may be used to arrive at a final derivative, variant, or analog. Generally, these changes are done on a few nucleotides to minimize the alteration of the molecule. However, larger changes may be tolerated in certain circumstances.

Generally, the nucleotide identity between individual variant sequences can be at least 90%, 91%, 92%, 93%, 94%, 95%, 96%, 97%, 98%, 99%, or 100%. Thus, a "variant sequence" can be one with the specified identity to a parent or reference sequence (e.g. wild-type sequence) of the invention that comprises one or more amino acid alterations, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. In some aspects, a variant targeting peptide can be a sequence that contains 1, 2, 3, 4, or more amino acid base changes as compared to the parent or reference sequence of the invention, and shares or improves biological function, specificity and/or activity of the parent sequence. Thus, a variant targeting peptide can be one with the specified identity to the parent sequence of the invention (e.g. SEQ ID NO:1), and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. The variant sequence can also share at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of a reference sequence (e.g. SEQ ID NO:1).

The terms "variant" and "mutant" or "modified" can be used interchangeably. As used herein, the term "variant" refers to a modified nucleic acid or protein which displays the same characteristics when compared to a reference nucleic acid or protein sequence. A modified targeting peptide can be at least 65, 70, 75, 80, 85, 90, 95, or 99 percent homologous to a reference sequence. In some aspects, a reference sequence can be SEQ ID NO:1. Variants can also include nucleotide sequences that are substantially similar to sequences disclosed herein. A "variant" or "variant thereof" can mean a difference in some way from the reference sequence other than just a simple deletion of an N- and/or C-terminal amino acid residue or residues. Where the variant includes a substitution of an amino acid residue, the substitution can be considered conservative or non-conservative. Variants can include at least one substitution and/or at least one addition, there may also be at least one deletion. Variants can also include one or more non-naturally occurring residues.

As used herein an amino acid "substitution" refers to the replacement of one amino acid residue by a different amino acid residue. The substituted amino acid may be any of the 20 amino acids commonly found in human proteins, as well as atypical or non-naturally occurring amino acids. A substitution of an amino acid residue can be considered conservative or non-conservative. Conservative substitutions are those within the following groups: Ser, Thr, and Cys; Leu, ILe, and Val; Glu and Asp; Lys and Arg; Phe, Tyr, and Trp; and Gln, Asn, Glu, Asp, and His. In some aspects, the substitution can be a non-naturally occurring substitution. For example, the subsitution may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art.

The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Antigen Delivery System

Disclosed is an immunotherapy based on an antigen delivery system to facilitate presentation of non-cancer HLA class 1 restricted immunogenic peptides in cancer cells, resulting in a secondary immune response against the cancer cells. The disclosed immunotherapy bypasses the need to identify tumor-associated antigens or to generate a primary immune response against the tumor, which are major hurdles in cancer vaccine development. Unlike immunomodulators, the immune response generated by the disclosed antigen delivery systems is antigen specific and does not involve an overall general activation of the immune response. This can minimize problems with autoimmune and off-target effects.

Disclosed are targeted nanoparticles used to deliver an antigen (e.g. viral antigen) for antigen presentation in cells (e.g. cancer cells). Disclosed are synthetic antigen delivery systems that are suitable for specific delivery of antigenic cargo into cells.

In some aspects, the disclosed antigen delivery system comprises a targeting peptide, a nanoparticle, and an HLA class I restricted peptide, each of the elements are described herein.

In some aspects, the antigen delivery system does not comprise any viral particles, toxins, or biologically-derived material. Thus, safety concerns are reduced in the disclosed antigen delivery systems.

Disclosed are antigen delivery systems comprising a nanoparticle, wherein the nanoparticle is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1). An example of the disclosed antigen delivery systems, is an antigen delivery system comprising a PEGylated liposome, wherein the PEGylated liposome is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

1. Targeting Peptide

Disclosed are antigen delivery systems comprising a nanoparticle wherein the nanoparticle is surface-modified with a targeting peptide. For example, disclosed are antigen delivery systems comprising a liposome, wherein the liposome is surface-modified with a cancer-specific cell targeting peptide.

In some aspects, the targeting peptides are cell-specific targeting peptides. In some aspects, the targeting peptides are cancer cell-specific targeting peptides. Disclosed are cancer-specific cell targeting peptides. In some non-limiting examples, the cancer-specific cell targeting peptide targets lung cancer, pancreatic cancer, breast cancer and/or glioblastoma.

Targeting peptides are well known and have been used in the past to target nanoparticles to a cell type. One particular targeting peptide, LQWRRDDNVHNFGVWARYRL (SEQ ID NO:2), is a cancer-specific cell targeting peptide but it has been found to be less effective for use in the disclosed antigen delivery systems due to its hydrophobic, difficult to purify, and unstable properties. Disclosed herein is a targeting peptide wherein amino acids 6-10 of SEQ ID NO:2 have been removed and the C- and N-terminus have been fused together resulting in a targeting peptide with increased cell binding and better physiochemical properties than the peptide of SEQ ID NO:2. Thus, in some aspects, the resulting targeting peptide comprises the amino acid sequence of LQWRRNFGVWARYRL (SEQ ID NO:1). In some aspects, the decreased hydrophobicity of SEQ ID NO:1 dramatically increased solubility and stability of the peptide, thus improving coupling to a nanoparticle, such as a liposome.

Disclosed are targeting peptides comprising the amino acid sequence of LQWRRNFGVWARYRL (SEQ ID NO:1). In some aspects, the targeting peptide comprising the amino acid sequence of SEQ ID NO:1 is a cancer-specific cell targeting peptide.

In some aspects, the disclosed targeting peptides specifically accumulate in cancer cells and facilitate HLA class I presentation.

In some aspects, the targeting peptides can be conjugated to the surface of a nanoparticle, such as a liposome, using any techniques known in the art. For example, the targeting peptides can be conjugated to the surface of a liposome by a thiol-ester linkage resulting from a Michael addition of a single sulfhydryl group on the targeting peptide to the maleimide present on the liposome. In some aspects, the targeting peptides can be conjugated to the surface of a nanoparticle using amid chemistry and/or click chemistry.

In some aspects, the targeting peptides can be acetylated on the N-terminus. In some aspects, the targeting peptides can comprises a linker on the C-terminus. For example, in some aspects, the linker can be a PEG linker.

In some aspects, the disclosed antigen delivery systems can comprise a dimer of the disclosed targeting peptides, also called a targeting peptide dimer. In some aspects of the disclosed antigen delivery systems, the cancer-specific cell targeting peptide is a dimer, wherein at least one of the two targeting peptides comprises the sequence LQWRRNFGVWARYRL (SEQ ID NO:1). In some aspects, both of the targeting peptides in the dimer comprise the sequence LQWRRNFGVWARYRL (SEQ ID NO:1). In some aspects, the targeting peptide dimer is connected via a linker, such as PEG, and a branch point. In some aspects, the branch point can be a lysine residue. For example, in some aspects, the dimer comprises the sequence (SEQ ID NO: 3)
(CH3CO-LQWRRNFGVWARYRL-PEG11)$_2$K In some aspects, there are at least two linkers, one on the end of each targeting peptide. In some aspects, two or more linkers can be used. In some aspects, the linker can be PEG11. In some aspects, more or less ethylene glycol subunits can be used. For example, the PEG can have between 2 to 24 ethylene glycols.

In some aspects, the targeting peptide dimer can further comprise a conjugation moiety on the C-terminal side of the branch point, wherein the conjugation moiety allows for conjugation to the liposome. For example, in some aspects, the dimer comprises the sequence (CH3CO-LQWRRNFGVWARYRL-PEG11)$_2$K-X (SEQ ID NO:4), wherein X is a tag or reactive moiety for conjugation.

In some aspects, the disclosed targeting peptides can facilitate HLA class I presentation using autophagy. In some aspects, the disclosed targeting peptides can accumulate in autophagic vesicles in cells. The accumulation of the targeting peptides in autophagic vesicles leads to accumulation of the entire antigen delivery system in autophagic vesicles which can result in presentation of the HLA class I restricted peptide of the antigen delivery system.

In some aspects, the targeting peptide can comprise a sequence having at least 75, 80, 85, 90, 95, 99% identity to SEQ ID NO:1. Thus, variants of SEQ ID NO:1 are disclosed herein and can be used in the disclosed antigen delivery systems.

2. Nanoparticle

Disclosed are antigen delivery systems comprising a nanoparticle wherein the nanoparticle is surface-modified with a targeting peptide. In some aspects, the nanoparticle can be any vehicle with the capacity to carry cargo, specifically a peptide, without modifying the cargo. In some aspects, the vehicle needs to have high payload capacity and shield the immunogenic peptide cargo without modification as presentation in HLA class I molecules is restricted by size and position of amino acid residues.

In some aspects, a nanoparticle can be inorganic, liposome, virus-like particle, or polymeric. A variety of materials exist from which nanoparticles can be synthesized. Examples of such materials can be, but are not limited to, lipids (viral envelop or phospholipids), synthetic polymers such as poly(allylamine hydrochloride) (PAH), poly(acrylic acid) (PAA) and poly(methacrylic acid) (PMA), poly(lactide-co-glycolide) (PLGA), and polypeptides such as poly-L-lysine (PLL), natural polymers such as chitosan, and proteins such as albumin.

In some aspects, the disclosed antigen delivery systems comprise a liposome. In some aspects, liposomes are self-assembling phospholipid bilayers with an aqueous core. In some aspects, liposomes can be fabricated in a multilayered structure; therefore, they can allow the encapsulation of both hydrophilic and hydrophobic antigens between different layers. Liposomes can be readily manufactured from synthetic material, easily loaded with synthetic peptide, and amenable to modification with targeting peptides. In some aspects, liposomes accumulate passively in tumors based on the enhanced permeability and retention effect, thus, enhancing the specificity of the treatment. In some aspects, nanoparticles can be metallic, organic, inorganic and polymeric nanostructures, including dendrimers, micelles, and liposomes.

In some aspects, the disclosed antigen delivery systems comprise a PEGylated liposome. A PEGylated liposome comprises the synthetic polymer poly-(ethylene glycol) (PEG). In some aspects, the presence of PEG on the surface of the liposome can extend blood-circulation time while reducing mononuclear phagocyte system uptake. Thus, in some aspects, PEGylated liposomes are also known as stealth liposomes. In some aspects, DSPE PEG2000 modified with maleimide can be incorporated into the lipid formulation of a liposome allowing for conjugation of a thiol containing targeting peptide to the liposome.

In some aspects, the liposomes can be between 30 nm and 350 nm. In some aspects, the liposomes can be about 100 nm. Disclosed are 100 nm stealth liposomes that encapsulate a synthetically manufactured immunogenic peptide.

In some aspects, the nanoparticles can further comprise a detectable label. In some aspects, the detectable label can be a chemiluminescent label, fluorescent label, or enzymatic label. As used herein, a "detectable label" is a nucleic acid, protein, or compound that can be detected or can lead to a detectable response. Detectable labels in accordance with the invention can be conjugated, either directly or indirectly, to a nanoparticle or encapsulated within a nanoparticle and include radioisotopes, enzymes, haptens, chromophores such as dyes or particles that impart a detectable color (e.g., latex beads or metal particles), luminescent compounds (e.g., bioluminescent, phosphorescent or chemiluminescent moieties), a quantum dot, and fluorescent compounds, such as fluorescent proteins.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrapel, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

In some aspects, the nanoparticles are conjugated to the targeting peptides described herein using methods known in the art.

In some aspects, the nanoparticles encapsulate, or are loaded with, one or more of the HLA class I restricted peptides described herein. In some aspects, the nanoparticles comprises one or more of the same HLA class I restricted peptide. For example, a nanoparticle can encapsulate 1, 2, 3, 4, 5, 6, 7, 8, 9, 10 or more of a single HLA class I restricted peptide described herein. In some aspects, the nanoparticles comprises one or more of the same HLA class I restricted peptide but a nanoparticle comprising one HLA class I restricted peptide and a nanoparticle comprising a different HLA class I restricted peptide can both be used in the disclosed antigen delivery system. For example, using more than one HLA class I restricted peptide in the antigen delivery system but each HLA class I restricted peptide is in its own nanoparticle.

3. HLA Class I Restricted Peptide

HLA class I molecules are found on the surface of all nucleated cells of vertebrates. In some aspects, HLA class I molecules function to present or display peptide fragments to cytotoxic T cells. In some aspects, HLA class I molecules present peptides from inside of a cell (i.e. endogenous peptides). In some aspects, HLA class I molecules comprise a class I peptide binding groove that accommodates a processed peptide of 8 to 10 amino acid residues or, on some occasions, 11-14 amino acids, known as a HLA class I restricted peptide. Thus, in some aspects, the disclosed HLA class I restricted peptides are 8-14 amino acids in length. In some aspects, the disclosed HLA class I restricted peptides are 8-10 amino acids in length.

In some aspects, the disclosed HLA class I restricted peptides can be a peptide that a subject has been previously exposed to. For example, the peptide can be derived from a virus, bacteria or fungus that a subject was previously exposed to (infected with). In some aspect, the peptide can be derived from a peptide a subject was previously exposed to via vaccination. Thus, in some aspects, the disclosed HLA class I restricted peptides can be vaccine-dependent, immunogenic HLA class I restricted peptide. In some aspects, a vaccine-dependent, immunogenic HLA class I restricted peptide means that the HLA class I restricted peptide is derived from a vaccine used to previously immunize a subject that is receiving one of the disclosed antigen delivery systems. For example, if a subject has been vaccinated with an influenza vaccine, a vaccine-dependent, immunogenic HLA class I restricted peptide can be a peptide derived from the influenza vaccine. Vaccine-dependent means the HLA class I restricted peptide is derived from a vaccine comprising that peptide and wherein the subject receiving the antigen delivering system comprising the HLA class I restricted peptide has already been vaccinated with the vaccine. Secondary immunogenic means the HLA class I restricted peptide induces a secondary immune response to the HLA class I restricted peptide. For example, the HLA class I restricted peptide induces a secondary immune response because it is a vaccine-dependent HLA class I restricted peptide and therefore a subject has already been vaccinated and generated a primary immune response against the peptide. In some aspects, a secondary immune response is more rapid and efficient.

Do to the previous exposure to the HLA class I restricted peptide, the peptide can also be referred to as a previous immune response-dependent, secondary immunogenic HLA class I restricted peptide. For example, disclosed are vaccine-dependent, secondary immunogenic HLA class I restricted peptide. Previous immune response-dependent, or vaccine-dependent can mean the subject has previously generated an immune response to the HLA class I restricted peptide and therefore it is secondary immunogenic because an immune response generated to the HLA class I restricted peptide in this delivery system is a secondary immune response.

In some aspects, a vaccine-dependent, immunogenic HLA class I restricted peptide can be any HLA class I restricted peptide derived from a vaccine comprising that peptide. In some aspects, a vaccine-dependent, immunogenic HLA class I restricted peptide can be measles virus hemagglutinin peptide H250. In some aspects, a vaccine-dependent, immunogenic HLA class I restricted peptide can be influenza virus hemagglutinin peptide HA. In some aspects, a vaccine-dependent, immunogenic HLA class I restricted peptide can be smallpox virus H-2Kd-restricted vaccinia-specific peptide, A5275-83 (VACV-A52). In some aspects, a vaccine-dependent, immunogenic HLA class I restricted peptide can be H250 (SMYRVFEVGV; SEQ ID NO:5), C166 (SLWGSLLML; SEQ ID NO:6), H38 (LLAV-IFVMFL; SEQ ID NO:7), H516 (ILPGQDLQYV; SEQ ID NO:8), H3L (SLSAYIIRV; SEQ ID NO:9), E2L (KIDYYIPYV; SEQ ID NO:10), or 01L (GLNDYLHSV; SEQ ID NO:11).

In some aspects, the HLA class I restricted peptide can be based on the specific HLA type of a subject receiving the disclosed antigen delivery systems.

4. Therapeutic

In some aspects, the nanoparticles of the disclosed antigen delivery systems can be further loaded with a therapeutic. Therefore, a cell would receive both the HLA class I restricted peptide and a therapeutic from the nanoparticle.

In some aspects, the therapeutic is a cancer therapeutic. In some aspects, a cancer therapeutic can be any known cancer therapeutic. In some aspects, a cancer therapeutic can be, but is not limited to, methotrexate, docetaxel-gemcitabine, bevacizumab, cyclophosphamide, erlotinib, gemcitabine, crizotinib, atezolizumab, nivolumab, pembrolizumab, estrogen modulator, hormone based chemotherapy, fluorouracil, oxaliplatin, irinotecan, leucovorin, carmustine, temozolomide.

In some aspects, the therapeutic is a drug that induces autophagy. Because autophagy can be important for antigen presentation, delivering a drug that induces autophagy in combination with an HLA class I restricted peptide can increase the efficacy of the HLA class I restricted peptide being presented. In some aspects, drugs that induce autophagy can be, but are not limited to, L-type Ca2+ channel blockers (verapamil, loperamide, amiodarone), calpain inhibitors (calpastatin), ATP-sensitive K+ channel agonist (minoxidil), cAMP reducing agents (rilmenidine, clonidine), inositol lowering agents (valproic acid), inhibitors against class I PI3K (LY294002), mTOR (rapamycin), AKT (perifosine), and IMPase (Li+).

C. Compositions

Disclosed are compositions comprising the disclosed antigen delivery systems. For example, disclosed are compositions comprising an antigen delivery system, wherein the antigen delivery system comprises a nanoparticle, wherein the nanoparticle is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

1. Pharmaceutical Compositions

In some aspects, the disclosed compositions can be pharmaceutical compositions.

For example, in some aspects, disclosed are pharmaceutical compositions comprising a composition comprising one or more of the antigen delivery systems disclosed herein and a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, or conjugate of the invention is not compromised. Pharmaceutical compositions may also include one or more active ingredients (in addition to the composition of the invention) such as antimicrobial agents, anti-inflammatory agents, anesthetics, and the like.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the fusion proteins. Thus, compositions can be prepared for parenteral administration that includes fusion proteins dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The pharmaceutical compositions described above can be formulated to include a therapeutically effective amount of a composition disclosed herein. In some aspects, therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to one or more autoimmune diseases or where the patient has a clinically determined predisposition or increased susceptibility (in some cases, a greatly increased susceptibility) to cancer.

The pharmaceutical compositions described herein can be administered to the subject (e.g., a human subject or human patient) in an amount sufficient to delay, reduce, or preferably prevent the onset of clinical disease. Accordingly, in some aspects, the subject is a human subject. In therapeutic applications, compositions are administered to a subject (e.g., a human subject) already with or diagnosed with cancer in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the autoimmune disease or a symptom of the autoimmune disease is ameliorated. One or more of the symptoms can be less severe. Recovery can be accelerated in an individual who has been treated.

The total effective amount of the conjugates in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The pharmaceutical composition may be administered in a number of ways depending on whether local or systemic treatment is desired, and on the area to be treated.

D. Methods of Treating

Disclosed are methods of treating a subject having cancer comprising administering one of the antigen delivery systems disclosed herein to a subject having cancer. In some aspects, the subject is first diagnosed with cancer and then administered one of the antigen delivery systems disclosed herein.

Disclosed are methods of treating a subject having cancer comprising administering an antigen delivery system comprising a nanoparticle, wherein the nanoparticle is surface-modified with a cancer-specific cell targeting peptide and comprises an immunogenic HLA class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1). For example, disclosed are methods of treating a subject having cancer comprising administering an antigen delivery system comprising a PEGylated liposome, wherein the PEGylated liposome is surface-modified with a cancer-specific cell targeting peptide and comprises an immunogenic human leukocyte antigen (HLA) class I restricted peptide, wherein the HLA class I restricted peptide is a vaccine-dependent, immunogenic HLA class I restricted peptide, and wherein the cancer-specific cell targeting peptide comprises the sequence LQWRRNFGVWARYRL (SEQ ID NO:1).

In some aspects, the antigen delivery system is targeted to a cancer cell in the subject, wherein, upon entry of the liposome into the cancer cell in the subject, the cancer cell presents the vaccine-dependent, immunogenic HLA class I restricted peptide from the antigen delivery system on its surface in HLA class I molecules, and wherein the subject generates an immune response to the vaccine-dependent, immunogenic HLA class I restricted peptide. In other words, the nanoparticle, such as a liposome, along with the targeting peptide (e.g. peptide comprising LQWRRNFGVWARYRL (SEQ ID NO:1)), help get the HLA class I restricted peptide inside of a cancer cell wherein the cancer cell can then present the HLA class I restricted peptide in a manner that generates an immune response to the HLA class I restricted peptide. In some aspects of the disclosed methods, the immune response to the vaccine-dependent, immunogenic antigen targets and kills cancer cells presenting the vaccine-dependent, immunogenic antigen.

In some aspects of the disclosed methods, the cancer-specific cell targeting peptide targets the nanoparticles (e.g. liposomes) to the cancer cells.

In some aspects, the disclosed methods can further comprise administering a therapeutic to the subject. In some aspects, the therapeutic is a cancer therapeutic. In some aspects, the cancer therapeutic can be a checkpoint inhibitor. In some aspects, the cancer therapeutic can be a chemotherapeutic agent. In some aspects, the therapeutic is an inducer of autophagy. In some aspects, the therapeutic is encapsulated in the nanoparticle, similar to the HLA class I restricted peptide. In some aspects, the therapeutic is administered separately from the nanoparticle.

In some aspects, the disclosed methods can further comprise detecting an immune response to the vaccine-dependent, immunogenic HLA class I restricted peptide in the subject. The step of detecting an immune response to the vaccine-dependent, immunogenic HLA class I restricted peptide in the subject can confirm that the treatment is effective. In some aspects, determining the immune response to the vaccine-dependent, immunogenic HLA class I restricted peptide in the subject can be an important factor in determining what the best vaccine-dependent, immunogenic HLA class I restricted peptide is to use in the antigen delivery system.

In some aspects, a subject is first HLA typed prior to treatment. HLA typing can allow for identifying which HLA class I restricted peptides to use in the antigen delivery system.

E. Methods of Killing Cancer Cells

Disclosed are methods of killing cancer cells comprising contacting cancer cells with any of the antigen delivery systems disclosed herein, wherein upon entry of the liposome into the cancer cells, the cancer cells present the vaccine-dependent, immunogenic HLA class I restricted peptide from the antigen delivery system, wherein the cancer cells generate an immune response to the vaccine-dependent, immunogenic HLA class I restricted peptide antigen, and wherein the immune response to the vaccine-dependent, immunogenic HLA class I restricted peptide antigen targets and kills the cancer cells presenting the vaccine-dependent, immunogenic HLA class I restricted peptide antigen. In some aspects, when a cancer cell presents the vaccine-dependent, immunogenic HLA class I restricted peptide it is intended to mean that the vaccine-dependent, immunogenic HLA class I restricted peptide is presented on HLA class I molecules on the surface of the cancer cell.

In some aspects, the methods can further comprise contacting the cancer cells with a therapeutic. In some aspects, the therapeutic is a cancer therapeutic. Thus, a combination therapy can be used including the disclosed antigen delivery system and a known cancer therapeutic. In some aspects, the cancer therapeutic is a checkpoint inhibitor. In some aspects, the cancer therapeutic can be, but is not limited to, chemotherapy, antibody therapy, immunotherapy, radiation therapy, hormone therapy, stem cell therapy, or targeted therapy. Any known cancer therapeutic can be used in combination with the antigen delivery system described herein.

In some aspects, the cancer cells are in a subject. Thus, in some aspects, the contacting of cancer cells with the antigen delivery system comprises administering the antigen delivery system to a subject.

F. Methods of Generating a Non-Cancer Secondary Immune Response

Disclosed are methods of generating a non-cancer secondary immune response that targets cancer cells comprising administering one of the antigen delivery systems disclosed herein to a subject having cancer cells, wherein, upon entry of the liposome into the cancer cell in the subject, the cancer cell presents the vaccine-dependent, immunogenic HLA class I restricted peptide from the antigen delivery system, wherein the subject generates a non-cancer secondary immune response to the vaccine-dependent, immunogenic HLA class I restricted peptide, wherein the non-cancer secondary immune response targets and kills the cancer cells presenting the vaccine-dependent, immunogenic HLA class I restricted peptide.

As described herein, a non-cancer secondary immune response is a secondary immune response to an antigen other than a cancer antigen. In some aspects, a non-cancer secondary immune response, although directed to an antigen other than a cancer antigen, can target cancer cells presenting a non-cancer antigen on its surface. Thus, as described herein, a non-cancer secondary immune response can target and kill cancer cells that present the non-cancer antigen. For example, cancer cells presenting a measles peptide (due to the antigen delivery system described herein) can generate a secondary immune response to the measles peptide resulting in killing of the cancer cells presenting the measles peptide.

In some aspects, a subject is first determined to have been vaccinated with a vaccine comprising the vaccine-dependent, immunogenic HLA class I restricted peptide.

In some aspects, a subject is first HLA typed prior to administering the antigen delivery system. HLA typing can allow for identifying which HLA class I restricted peptides to use in the antigen delivery system.

G. Methods of Increasing Specific Localization to Cancer Cells

Disclosed are methods of increasing specific localization to a cancer cell comprising administering any of the disclosed antigen delivery systems to a subject having cancer cells, wherein a majority of the nanoparticles (e.g. liposomes) localize to the cancer cells. Disclosed are methods of increasing specific localization to a cancer cell comprising administering any of the disclosed antigen delivery systems to a subject having cancer cells, wherein at least 50%, 60%, 70%, 80%, or 90% of the nanoparticles (e.g. liposomes) localize to the cancer cells.

In some aspects, there is less than 10%, 20%, 30%, or 40% non-specific localization of the nanoparticles.

H. Kits

The materials described above as well as other materials can be packaged together in any suitable combination as a kit useful for performing, or aiding in the performance of, the disclosed method or preparation of the disclosed antigen delivery system. It is useful if the kit components in a given kit are designed and adapted for use together in the disclosed method. For example disclosed are kits comprising a cancer-specific cell targeting peptide comprising the sequence LQWRRNFGVWARYRL (SEQ ID NO:1).

The kits also can contain a liposome or a vaccine-dependent, immunogenic HLA class I restricted peptide.

The disclosed kits can also include instructions for making or using the disclosed antigen delivery systems.

EXAMPLES

Utilizing a delivery ligand to facilitate HLA class I presentation has previously been achieved using Cholera or Shiga toxins fused to class 1 restricted immunogenic peptides (17-19). Yet, these toxins accumulate indiscriminately in cells and are not targeted specifically to cancer cells. A parental peptide, H1299.3, was found to selectively accumulate in cancer cells and demonstrates limited binding to normal human bronchial epithelial cells thus potentially providing a greater therapeutic treatment window (20,21).

The disclosed targeting peptide having the amino acid sequence of SEQ ID NO:1 is based off of parent peptide H1299.3 and has the same properties with increased solubility and stability.

Furthermore, manufacturing Cholera or Shiga toxin requires biological synthesis and concerns remain about immunogenicity of the toxin-carriers. In addition, the current work differs from hapten painting or antibody-recruiting strategies in which a targeting agent delivers a hapten to the cell surface, resulting in antibody recruitment. The disclosed immunotherapy is designed to directly activate T cells by specific presentation of HLA class I restricted antigens in cancer cells via an internalization mechanism rather than generating antibody-dependent cellular cytotoxicity from hapten immobilization on the cell surface.

In some aspects, the disclosed immunotherapy differs from current virus-based immunotherapies, as viral products or live viruses are not employed, reducing safety concerns associated with these types of therapies.

Cancer Immunotherapies designed to generate a cell-mediated immune response against tumors are emerging as frontline treatment options for cancer; however, concerns regarding efficacy, safety and cost efficacy have limited the use of these treatments. To address these weaknesses, an immunotherapy capable of delivering previously encountered antigenic peptides specifically to cancer cells and facilitating their presentation through the MHC class I pathway has been developed. An example of the immunotherapy utilizes a modular synthetic nanoparticle delivery system comprising three components: a neutral stealth liposome, encapsulated synthetic immunogenic HLA class I restricted peptides derived from measles virus (MV), and a tumor-targeting peptide (referred to as H1299.3 or SRI_MGS5_V1) on the external surface of the liposome. The targeting peptide results in accumulation of the liposomes specifically inside cancer cells and facilitates presentation of the MV-derived immunogenic peptides in HLA class I molecules. This system is referred to as TALL (Targeted Antigen Loaded Liposomes). Therefore, TALL can generate a secondary immune response specifically against the targeted tumor cells in a patient who has been previously vaccinated against or infected by MV. In short, the immunotherapy tricks the immune system into responding as though the cancer cell is infected with MV without the use of a viral particle. A significant reduction in tumor growth using TALL has been shown in aggressive LLC1 (lung) murine models. The outcome is a robust cytotoxic T lymphocyte (CTL) response specifically against the tumor. This approach has advantages over current immunotherapies: 1) It bypasses the need to identify tumor-associated antigens (TAA) or educate the immune system through a primary immune response; 2) It does not rely on a TAA and can be effective against tumors with a low mutational load.

Disclosed are optimization experiments of parental peptide LQWRRDDNVHNFGVWARYRL (SEQ ID NO:2) that, unfortunately, has proven to be hydrophobic, difficult to purify, and unstable. This made coupling to the liposomes problematic. For this peptide to become a clinically viable targeting agent, subsequent peptide optimization was required. The result was the identification of LQWRRNFGVWARYRL (SEQ ID NO:1).

There were there main aims of the current studies: Aim 1—Optimize immunogenic peptide payload of TALL using previously identified MHC class I restricted immunogenic peptides. Aim 2—Isolate and characterize new cancer-targeting ligands that specifically internalize into cancer cells and funnel into HLA class I pathway using phage display methodology. Aim 3—Assess anti-tumor efficacy of TALL in tumor models.

The rationale behind these aims was as follows. A single immunogenic peptide derived from measles virus has been used in previous studies. Addition of multiple immunogenic peptides can enhance the immune response against the tumor by activating additional memory T cells. The original system demonstrated efficacy of one targeting peptide. However, no one peptide is likely to bind to all tumors encountered in the clinic. Identifying multiple targeting ligands will expand the breadth of patients able to derive therapeutic benefit from TALL. The ultimate goal is to develop a clinically useful cancer treatment. Thus, in vivo anti-tumor efficacy studies are performed using mouse tumor models.

H250 has been previously utilized as an immunogenic peptide in the TALL system, which is HLA class I restricted and elicits a strong CD8 specific IFN$\gamma$ response in HLA A*02:01 patients. However, a multitude of peptides contribute to the immunogenic response elicited by the pathogen and it can be useful to expand the repertoire of antigenic peptides delivered by the disclosed system.

One of the objectives of the current study is to synthesize and add additional immunogenic peptides to the existing TALL system.

Using solid phase Fmoc chemistry, synthesis and purification was completed of the identified antigenic peptides derived from measles virus (MV) and vaccinia virus (VACV) shown in Table 1 in greater than 95% purity. These antigenic peptides bind to the HLA A*02:01 haplotype. MV and VACV are well-characterized pathogens which induce Th1 responses and have a high coverage of vaccination against the pathogen in the population. The H250 peptide was also synthesized with an AlexaFluor546 dye attached via a cysteine placed at the C-terminus of the peptide. This allows doping of a small amount to the labeled peptide into the liposome so that the liposome loading efficiency can be tracked and quantitated in vitro and in in vivo delivery of the antigenic peptide.

TABLE 1

| HLA class I (A*02:01) | | |
| --- | --- | --- |
| Gene Name | Peptide Sequence | Pathogen |
| H250 | SMYRVFEVGV | MV |
| C166 | SLWGSLLML | MV |
| H38 | LLAVIFVMFL | MV |
| H516 | ILPGQDLQYV | MV |
| H3L | SLSAYIIRV | VACV |
| E2L | KIDYYIPYV | VACV |
| O1L | GLNDYLHSV | VACV |

One objective was to improve the biophysical properties and biological properties of the parental sequence of (LQWRRDDNVHNFGVWARYRL (SEQ ID NO:2). This was achieved determining the minimal binding motif of LQWRRDDNVHNFGVWARYRL (SEQ ID NO:2), testing N-terminal and C-terminal modifications, and multimerizing the peptide on a scaffold.

Determining the minimal binding domain allows one to know where they can modify the peptide or even truncate the peptide without sacrificing functionality. Decreasing peptide length is also expected to reduce unwanted proteolysis and potential immune response and lessen the cost of synthesis of the targeting moiety while improving synthetic yields. Furthermore, it allows the focus to be on key regions of the peptide for improvement of solubility and stability. A set of four peptides were synthesized for each peptide sequence in which amino acids 1-5 (A1), 6-10 (A2), 11-15 (A3), or 16-20 (A4) were replaced by alanine (Table 2). Previous data indicated that the dimeric form of the parental peptide, SEQ ID NO:2, was the optimal valency. As such, each peptide was coupled to a lysine core containing a biotin tag to create the peptides shown in FIG. 1. Peptides were tested for binding to NSCLC lines using flow cytometry. Once the binding region was determined, a second round of peptides was made in which individual amino acids were changed to an alanine (Table 2).

LQWRRNFGVWARYRL-PEG11)$_2$K-X where X is a tag or reactive moiety for conjugation, referred to as SRI_MGS5_V2).

Figure 3:
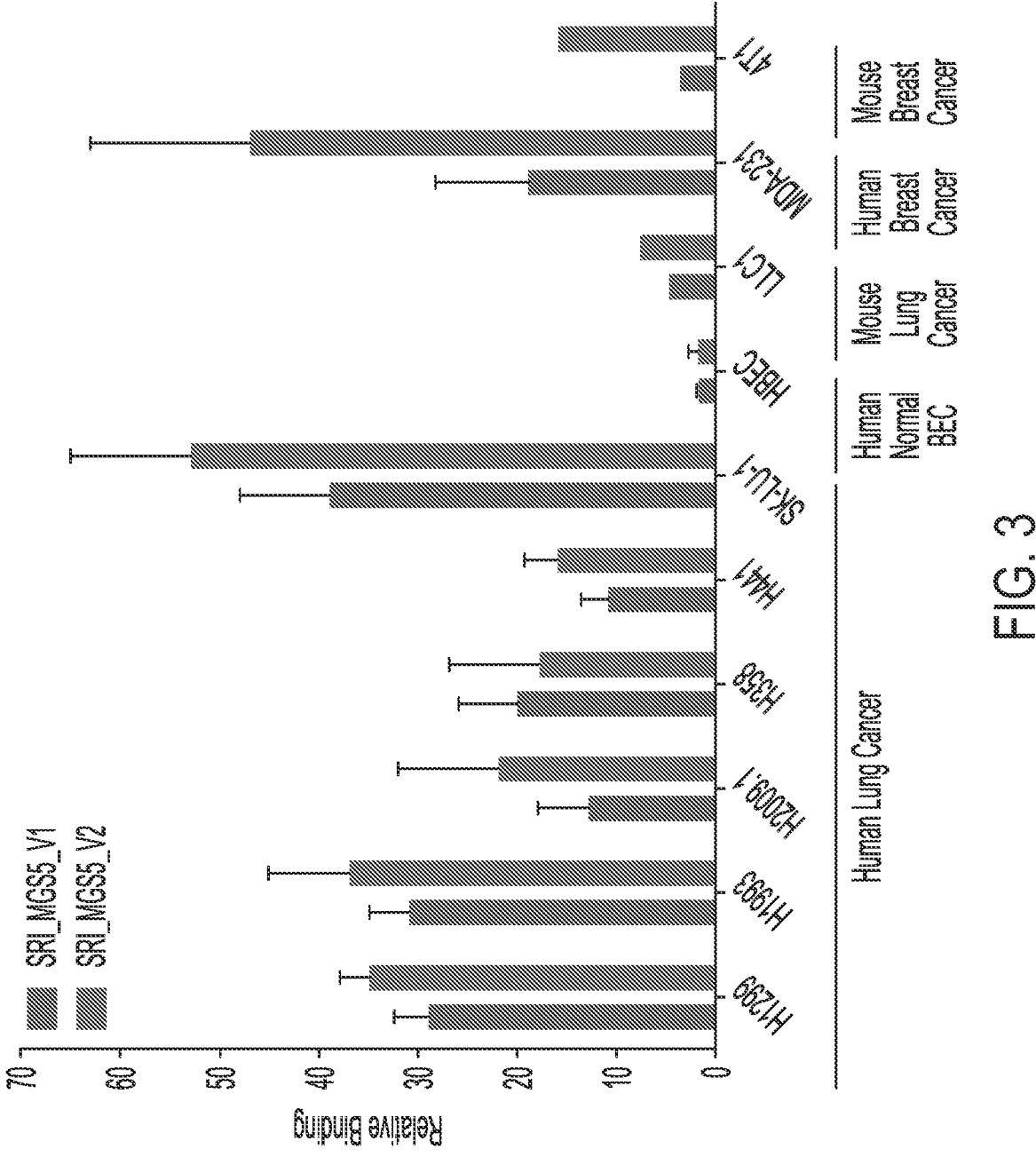
FIG.3 shows exemplary flow cytometry results showing increased binding of SRI_MGS5_V2 peptide on NSCLC lines compared to the parental peptide SRI_MGS5_V1.

The final optimized SRI_MGS5_V1 peptide, SRI_MGS5_V2, has the following characteristics. It is less hydrophobic compared to the parent peptide, which dramatically increased solubility and stability of the peptide thus improving coupling to the liposome and ease of handling. Flow cytometry data demonstrates that SRI_MGS5_V2 has greater binding affinity to several NSCLC lines when compared to the parental SRI_MGS5_V1 peptide, as shown in FIG. 3. Importantly, this data indicates that the SRI_MGS5_V2 binds to multiple NSCLC cell lines and is likely to have broad applicability in NSCLC (FIG. 3). Furthermore, SRI_MGS5_V2 has also been shown to bind to several breast cancer lines (MCF-7, MDA-MB-231and

TABLE 2

Alanine Scanning Sequences Synthesized and Tested for Cellular Binding

| MGS5 | Sequence | Full Monomer | Molecular Formula |
|---|---|---|---|
| FL | LQWRRDDNVHNFGVWARYRL | LQWRRDDNVHNFGVWARYRL-(PEG)11-Cys-CONH2 | C118H173N39O29 |
| A1 | AAAAADDNVHNFGVWARYRL | AAAAADDNVHNFGVWARYRL-(PEG)11-Cys-CONH2 | C99H145N31O28 |
| A2 | LQWRRAAAAANFGVWARYRL | LQWRRAAAAANFGVWARYRL-(PEG)11-Cys-CONH2 | C110H166N36O24 |
| A3 | LQWRRDDNVHAAAAAARYRL | LQWRRDDNVHAAAAAARYRL-(PEG)11-Cys-CONH2 | C102H161N37O28 |
| A4 | LQWRRDDNVHNFGVWAAAAA | LQWRRDDNVHNFGVWAAAAA-(PEG)11-Cys-CONH2 | C103H149N33O28 |
| 15 mer | LQWRRNFGVWARYRL | LQWRRNFGVWARYRL-(PEG)11-Cys-CONH2 | C95H141N31O19 |
| 10 mer | NFGVWARYRL | NFGVWARYRL-(PEG)11-Cys-CONH2 | C61H88N18O13 |
| A2.1 | LQWRRADNVHNFGVWARYRL | LQWRRADNVHNFGVWARYRL-(PEG)11-Cys-CONH2 | C117H173N39O27 |
| A2.3 | LQWRRDDAVHNFGVWARYRL | LQWRRDDAVHNFGVWARYRL-(PEG)11-Cys-CONH2 | C117H172N38O28 |
| A2.5 | LQWRRDDNVANFGVWARYRL | LQWRRDDNVANFGVWARYRL-(PEG)11-Cys-CONH2 | C115H171N37O29 |
| G2 | LQWRRGGGGGNFGVWARYRL | LQWRRGGGGGNFGVWARYRL-(PEG)11-Cys-CONH2 | C105H156N36O24 |

Figure 2:
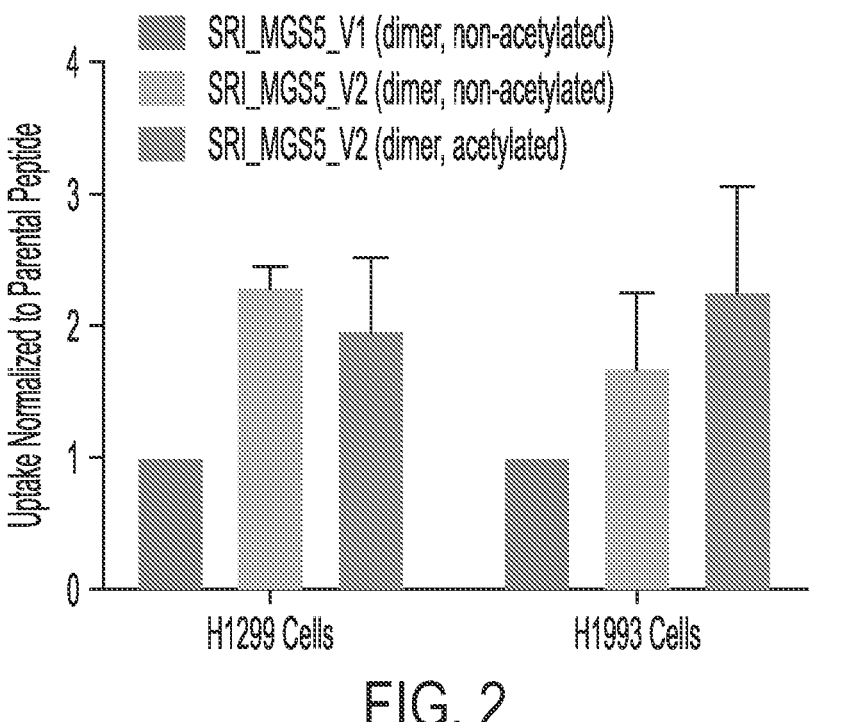
FIG. 2 shows an example of relative binding of acetylated vs non-acetylated SRI_MGS5 peptides on H1993 and H1299 cells. SRI_MGS5 are targeting peptides having the sequence LQWRRDDNVHNFGVWARYRL (SEQ ID NO:2) or derived from SEQ ID NO:2. For example, SRI_MGS5_V1 is a dimer comprising LQWRRDDNVHNFGVWARYRL (SEQ ID NO:2) and SRI_MGS5_V2 is a dimer comprising LQWRRNFGVWARYRL (SEQ ID NO:1).

Based on the alanine scanning results (shown in FIG. 1), it was determined that amino acids 1-5 and 11-20 contain key binding determinant. Single alanine substitutions within the 6-10 amino have no impact on peptide binding indicating this region does not contribute to binding and cellular uptake. The peptide comprised of only amino acids 11-20 did not bind to H1993 cells. Surprisingly, removal of amino acids 6-10 and fusing the C- and N-terminus of the parental peptide resulted in a peptide with increased cell binding and better physiochemical properties. The SRI_MGS5_V1 peptide was further improved by acetylating and dimerizing it on a branched lysine core (FIG. 2). The final optimized SRI_MGS5 peptide is comprised of 15 amino acids, an acetylated N-terminus, PEG11 linkers on the C-terminus to increase solubility and prevent aggregation and is dimerized on with a core that allows for further modification and attachment to the liposome: ((CH3CO- 4T1), pancreatic cancer line (Pan02) and glioma cell line (GL-261) (see FIGS. 28-33). The SRI_MGS5_V2 displays minimal binding to a normal control human lung epithelial cell line (HBEC, see FIG. 3). The peptide has high discriminating power between NSCLC cancer and normal cells in the lung.

Figure 4:
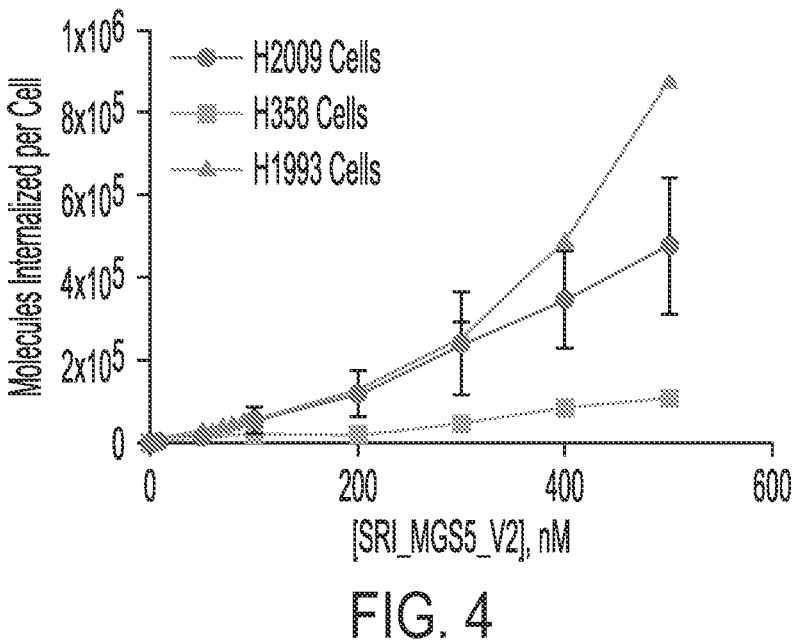
FIG. 4 shows an example of quantitative uptake of SRI_MGS5_V2 in three NSCLC cell lines at 1 H at varying concentrations. Uptake is represented as an average number of peptides per cell. Error bars are smaller than the symbol for some points.
Figure 5:
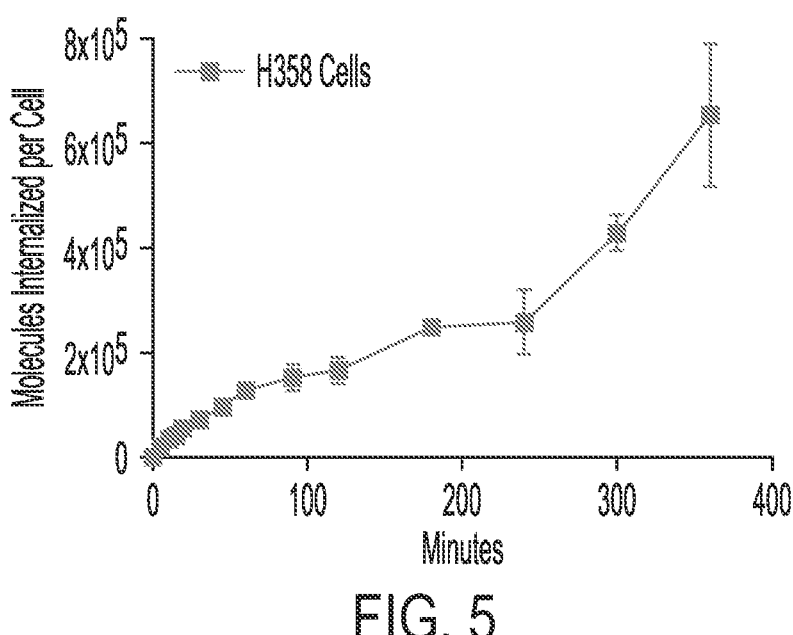
FIG. 5 shows exemplary flow cytometry results indicating the exact number of peptide molecules internalized by H358 NSCLC cell line over time when incubated 100 nM dye-labeled SRI_MGS2_V2. H358 cell line data has been not included in FIG. 6 for clarity due to differences in the Y axis.
Figure 6:
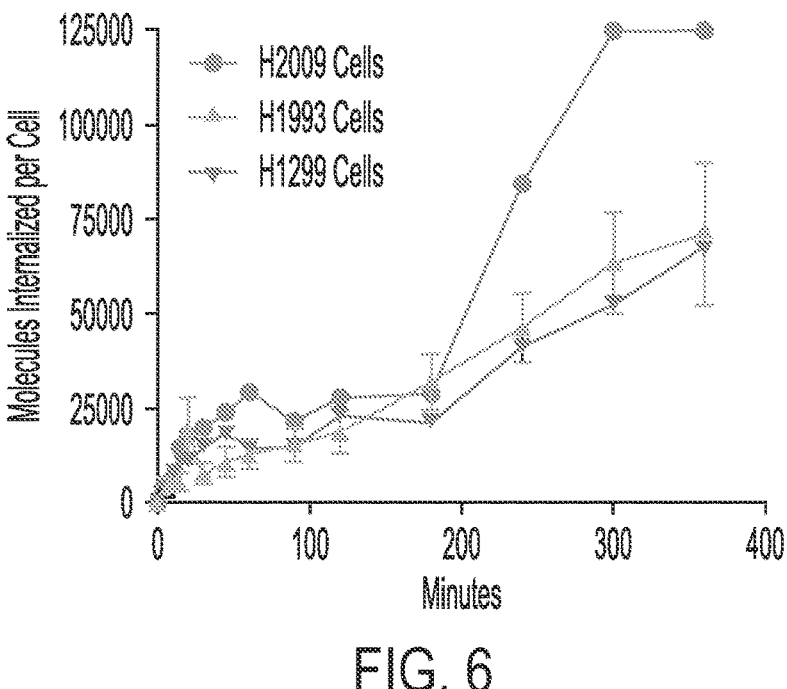
FIG. 6 shows exemplary flow cytometry results indicating the exact number of peptide molecules internalized by various NSCLC cell lines over time when incubated with 100 nM dye-labeled SRI_MGS5_V2.

A quantitative flow cytometry assay was performed that measures the average number of molecules of peptide internalized per cell. SRI_MGS5_V2 is internalized in three human NSCLC cell lines (FIG. 4). The number of molecules internalized ranges from $1\times10^5$ molecules/cell for H358 cells to $8\times10^5$ for H1993 cells, corresponding to intracellular concentrations of 100-800 nM. The rate of uptake at 6 hours is not saturated and it appears that peptide continues to enter the cell past this time (FIG. 5 and FIG. 6). This indicates either high receptor numbers which have not yet saturated or rapid recycling of the receptor that allows for continual delivery, reaching high intracellular concentrations of the peptide.

Uptake of SRI_MGS5_V2 is greatly reduced when the experiments are performed at 4° C., indicating that the binding and internalization is receptor mediated. Uptake of SRI_MGS5_V2 is not toxic to H1993 cells. No significant loss of viability is observed when cells are incubated SRI_MGS5_V2 for 72 hours at concentrations as high as 250 μM.

Figures 7A, 7B, 7C:
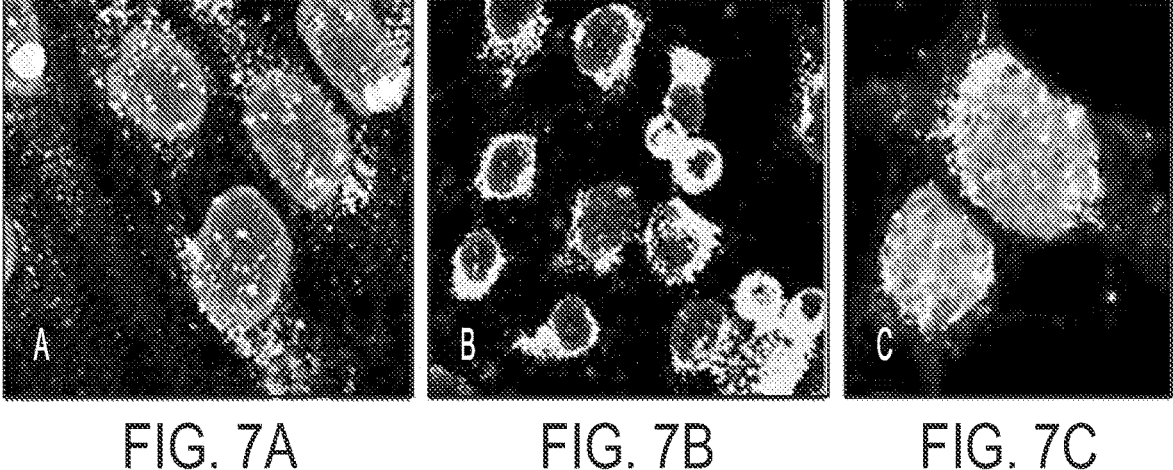
FIGS. 7A-7C show an example of co-localization of SRI_MGS5_V2 peptides with autophagic vesicles (A) H1993 cells treated with 100 nM of SRI_MGS5_V1 peptide (panel A) and optimized SRI_MGS_V2 (panels B and C) conjugated with Alexa Fluor 647 (Red). Autophagosomes are stained with LC3B antibody (Green). The regions corresponding to co-localization of the peptide and autophagic vesicles are shown in yellow.

Confocal microscopy results indicate that SRI_MGS5_V2 accumulates to a much greater extent in autophagic vesicles in H1993 NSCLC cells, when compared to the parental MGS5_V1 (FIG. 7). As indicated in the original proposal, SRI_MGS5_V1 facilitates MHC class I presentation of the antigenic peptide via an autophagy dependent mechanism, and treatment with autophagy inhibitors resulted in significant reduction in IFN-γ secretion. Therefore, accumulation in autophagosomes is a necessary component for success of this immunotherapy. Comparable results are observed in LLC1 cells.

Figure 8:
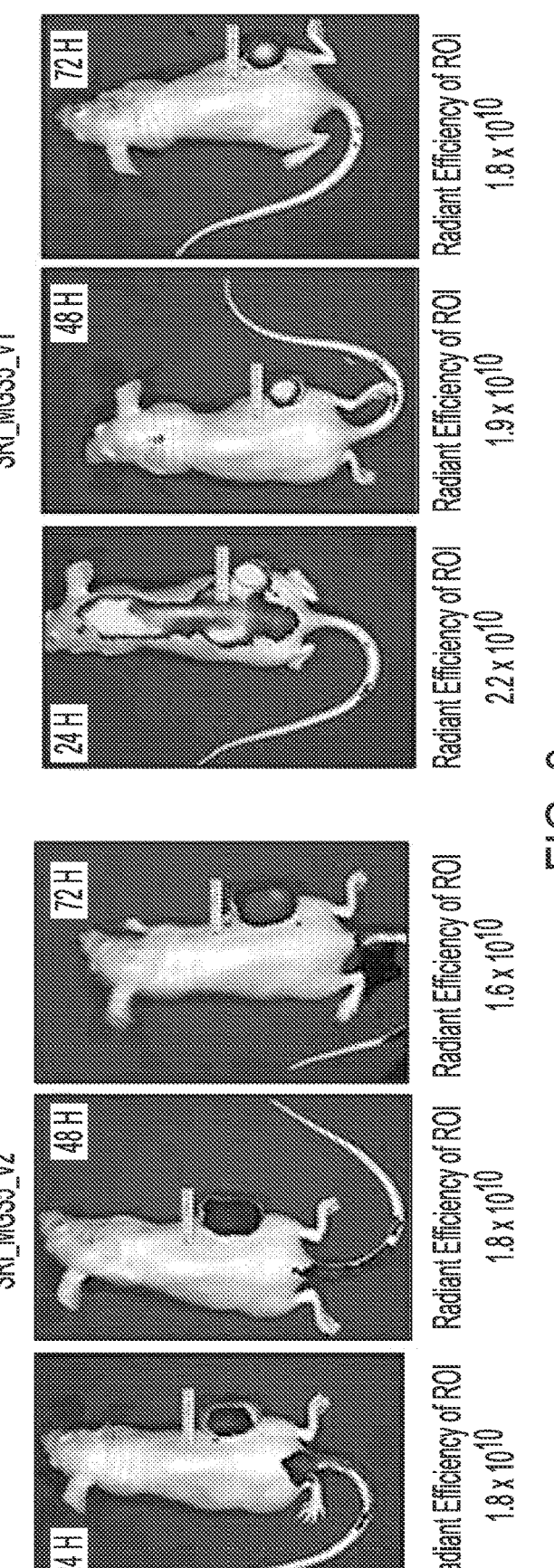
FIG. 8 shows exemplary near infrared (NIR) imaging results showing tumor accumulation of SRI_MGS5_V1 and SRI_MGS5_V2. The peptides were conjugated to Alexa Fluor 750 dye and 15 μs injected intravenously via the tail vein into mice bearing a subcutaneous H1993 NSCLC tumor on their right flank. Both peptides localize at the tumor site within 24 hours although SRI_MGS5_V1 shows significant signal along the dorsal side of the animal at 24 H. Signal is retained at 72 H.
Figure 9:
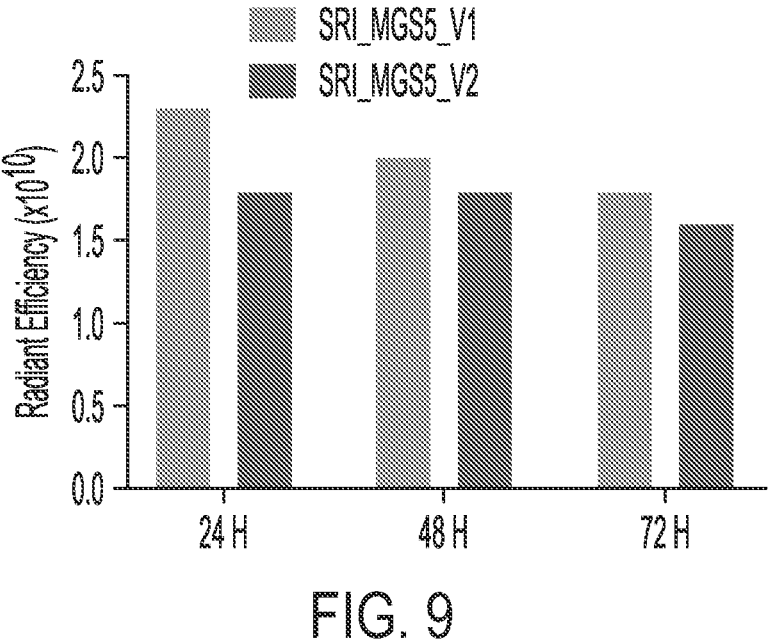
FIG. 9 shows an example of quantification of tumor uptake from in vivo images shown in FIG. 6. Both peptides show tumor targeting to the same extent.
Figure 10:
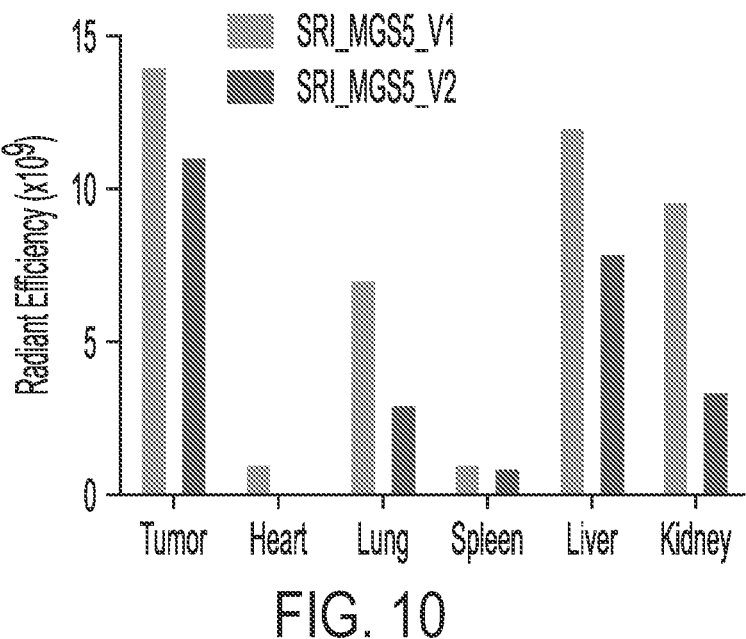
FIG. 10 Ex Vivo imaging of tumors and other organs at 72 H from experiment shown in FIG. 6.

SRI_MGS5_V2 and parental SRI_MGS5_V1 were labeled with the near-infrared dye Alexa Fluor 750 for imaging. After injection via the tail vein, the peptides accumulate specifically at the site of subcutaneous H1993 tumors to roughly the same degree and the signal is maintained for 72 hours, indicating that the peptide-dye conjugate is internalized (FIGS. 8 and 9). Ex vivo imaging at 72 H shows that SRI_MGS5_V2 has reduced non-specific accumulation in the lung and other organs when compared to the acetylated SRI_MGS5_V1 parental peptide, which is a desirable quality for NSCLC treatment. For example, SRI_MGS5_V2 has 3-fold lower signal in the lung compared to SRI_MGS5_V1. Similarly, SRI_MGS5_V2 displays 1.6-fold and 2.2-fold less signal in the liver and kidneys, respectively (FIG. 10). Importantly, the corresponding nonacetylated versions of each peptide were evaluated as well. No tumor targeting was observed for either nonacetylated peptide indicating the importance of protecting the N-terminus of the peptide for serum stability.

Figure 11:
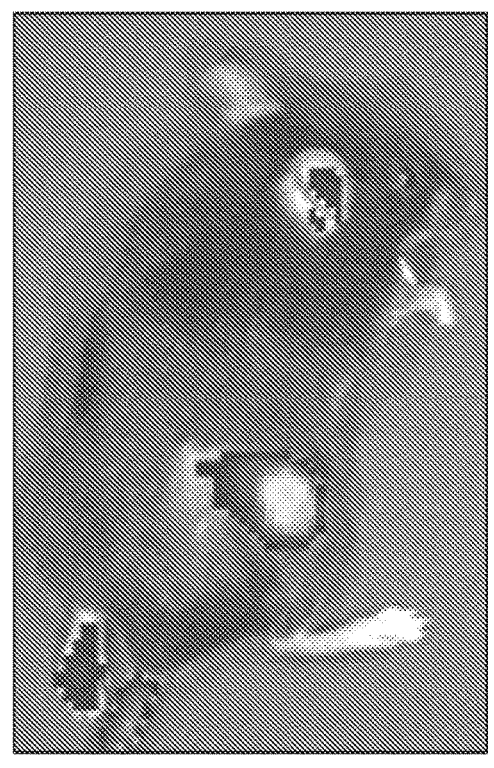
FIG. 11 shows an exemplary in vivo fluorescence image of the C57BL/6 mice 72 hours post injection with SRI_MGS5_V2 conjugated to Alexa Fluor 750 dye
Figure 12:
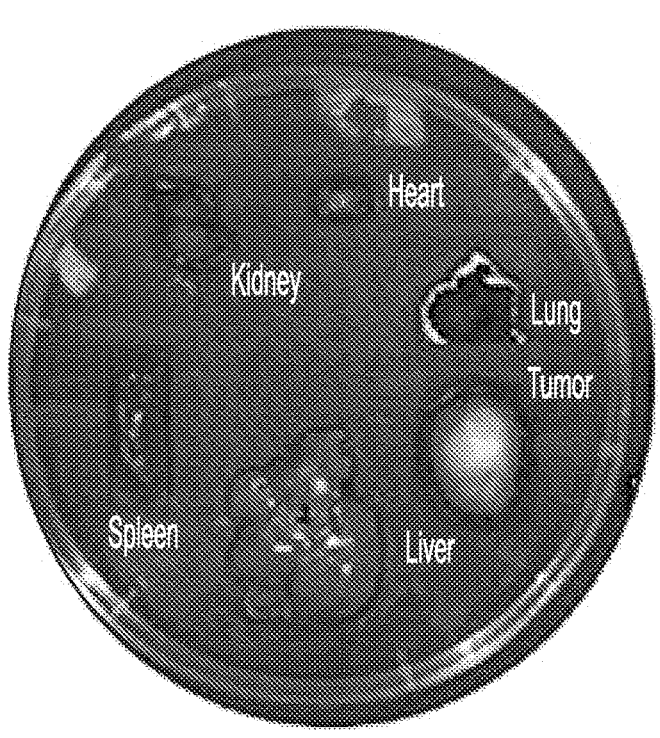
FIG. 12 shows an exemplary ex vivo fluorescence image of the organs obtained from the C57BL/6 mice 72 hours post injection with SRI_MGS5_V2 conjugated to Alexa Fluor 750 dye.
Figure 13:
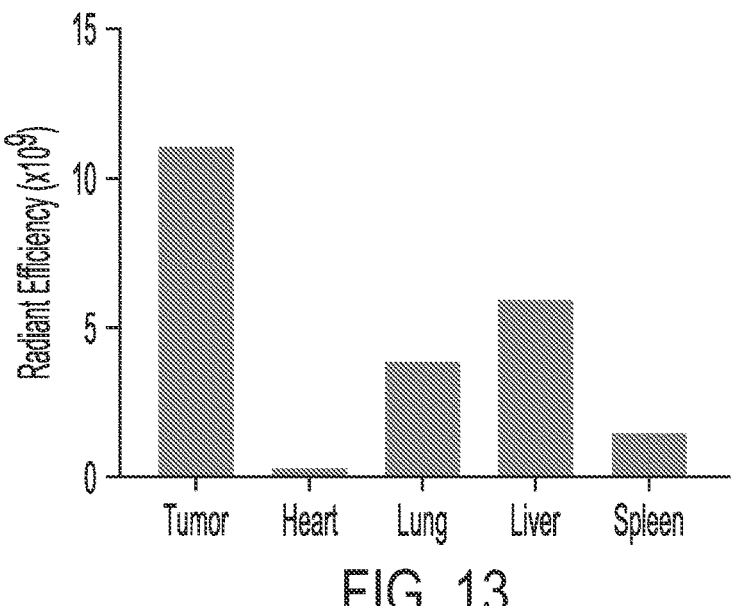
FIG. 13 shows Ex Vivo imaging of tumors and other organs at 72 H from experiment shown in FIGS. 11 and 12.

SRI_MGS5_V5 also homes to LLC1 tumors implanted subcutaneously in the hind flank of C57BL/6 mice (FIGS. 11-13). The LLC1 tumors were grown until palpable (≈500 mm³) at which point mice were treated I.V. with 15 μg of SRI_MGS5_V2 conjugated to Alexa Fluor 750. Images were taken daily for 72 hours, after which the animal was sacrificed, and its organs were assessed to determine localization of the targeting peptide. The results indicate that the SRI_MGS2_V2 successfully localized in the LLC1 tumor mass. As such, this peptide can be used for tumor targeting in syngeneic tumor models.

Liposome optimization was also studied. The liposomes were optimized by conjugation to SRI_MGS5_V2, which showed greater binding to NSCLC lines and localization within the autophagosomes of these cells. In order to optimize the TALL system, SRI_MGS5_V2 was conjugated to liposomes and the liposomes were characterized and utilized in co-culture assays to determine pro-inflammatory cytokine production.

Figure 14:
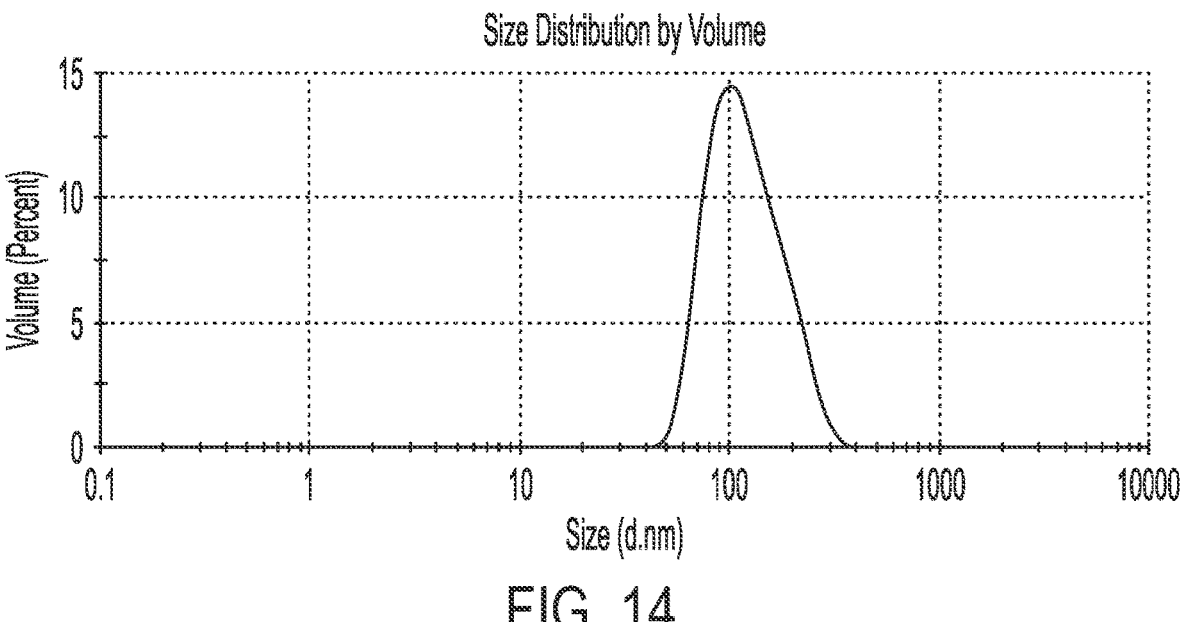
FIG. 14 shows the size distribution of the antigen loaded nanoparticles obtained via dynamic light scattering technique

The TALL system was made using the stealth liposome formulation used for DOXIL® but doping in 1.2% DSPE-PEG2000 maleimide allowing for conjugation of SRI_MGS5_V2. The size of the resulting liposome was determined to be ≈100 nm using dynamic light scattering (FIG. 14). To determine the loading efficiency, liposomes were loaded with fluorescently labeled antigenic peptides and treated with detergent which causes them to burst and releases their load. Fluorescence measurement post treatment with the detergent was used to estimate the loading efficiency of the liposome preparation technique. Antigenic peptide loading efficiency of the liposomes was determined to be 50% and is consistent from batch to batch.

Figure 15:
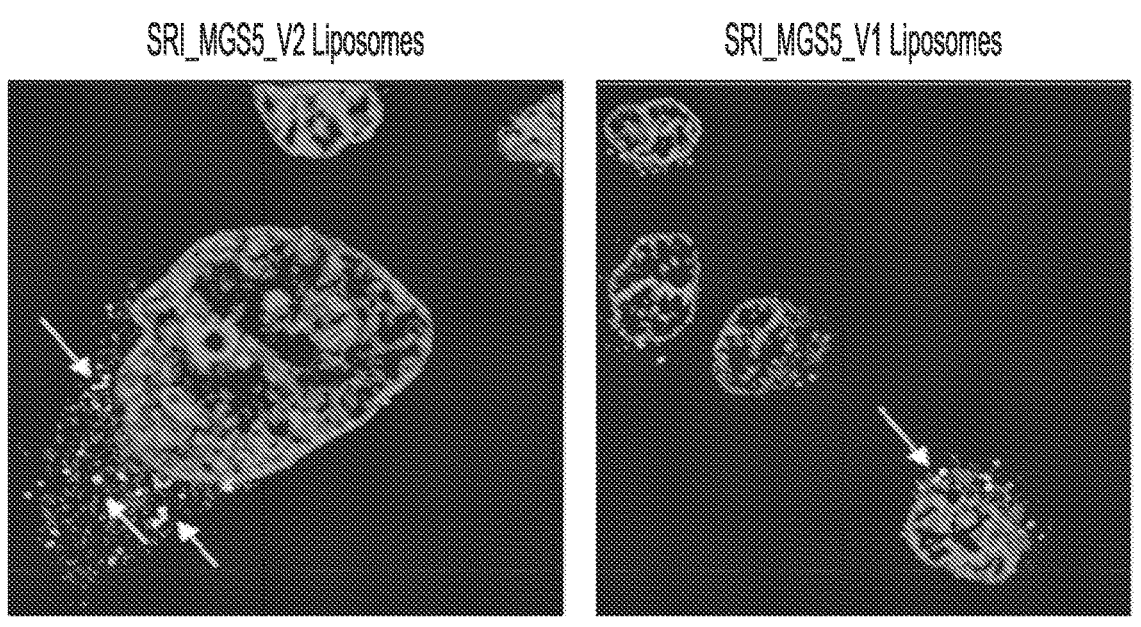
FIG. 15 shows an example of co-localization of autophagic vesicles with GFP-loaded nanoparticles conjugated to SRI_MGS5_V1 and SRI_MGS5_V2 peptides. The liposomes are loaded with GFP and appear green. Autophagosomes are stained with LC3B antibody (Red). The regions corresponding to co-localization of the liposomes and autophagic vesicles are shown in yellow.

To assure that SRI_MGS5_V2 targeted liposomes still trafficked to the autophagosome, green fluorescent protein (GFP) was encapsulated inside liposomes that was modified on the external surface with SRI_MGS5 variants. As shown in FIG. 15, clear co-localization of the liposomes with the autophagic vesicles is observed as indicated by the punctate yellow staining. While co-localization is observed for both peptides, again SRI_MGS5_V2 outperforms the parental peptide.

Figure 16:
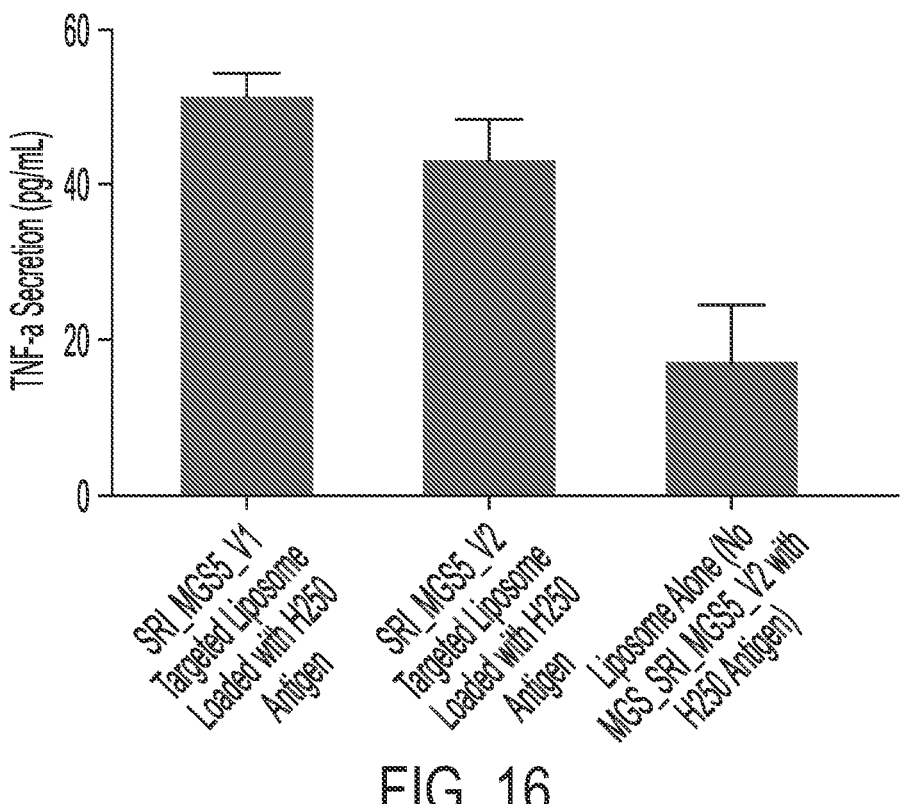
FIG. 16 shows exemplary TNF-α ELISA results indicating that SRI_MGS2_V2 targeting peptide facilitates presentation of encapsulated immunogenic peptide in HLA class I molecules. TALL treated H1993 cells were co-cultured with HLA-A2 positive PBMCs and culture supernatants were analyzed for TNF-α secretion. Concentration of all liposomes used in this assay corresponded to ≈4.5 mg/ml of phosphatidyl choline. Free H250 peptide control is incubated at 5 μmol/L.
Figure 17:
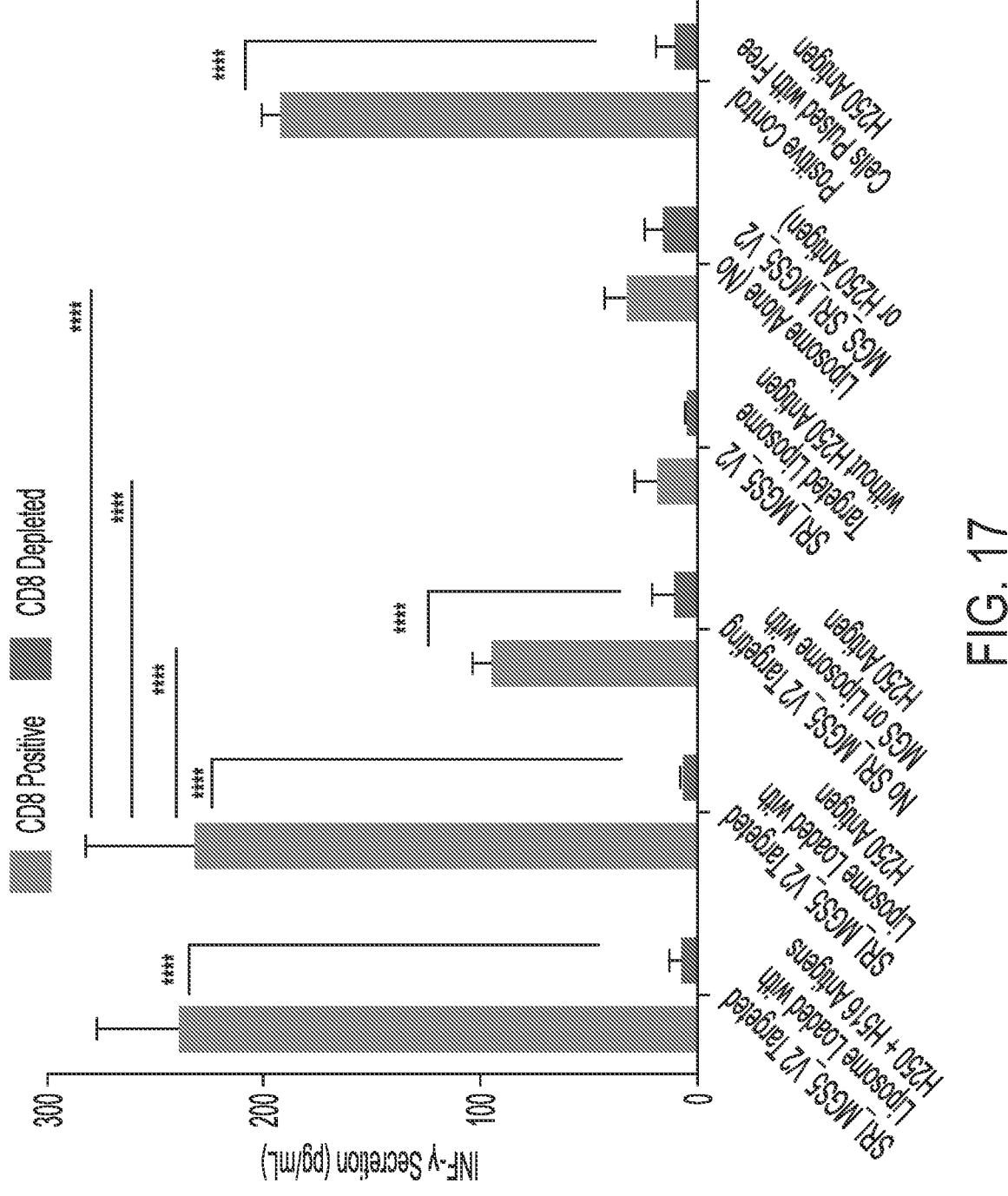
FIG. 17 shows exemplary IFNγ ELISA results indicating that SRI_MGS2_V2 targeting peptide facilitates presentation of encapsulated immunogenic peptide in HLA class I molecules. TALL treated H1993 cells were co-cultured with HLA-A2 positive PBMCs and culture supernatants were analyzed for IFNγ secretion. Concentration of all liposomes used in this assay corresponded to ≈4.5 mg/ml of phosphatidyl choline. Free H250 peptide control is incubated at 5 μmol/L.
Figure 18:
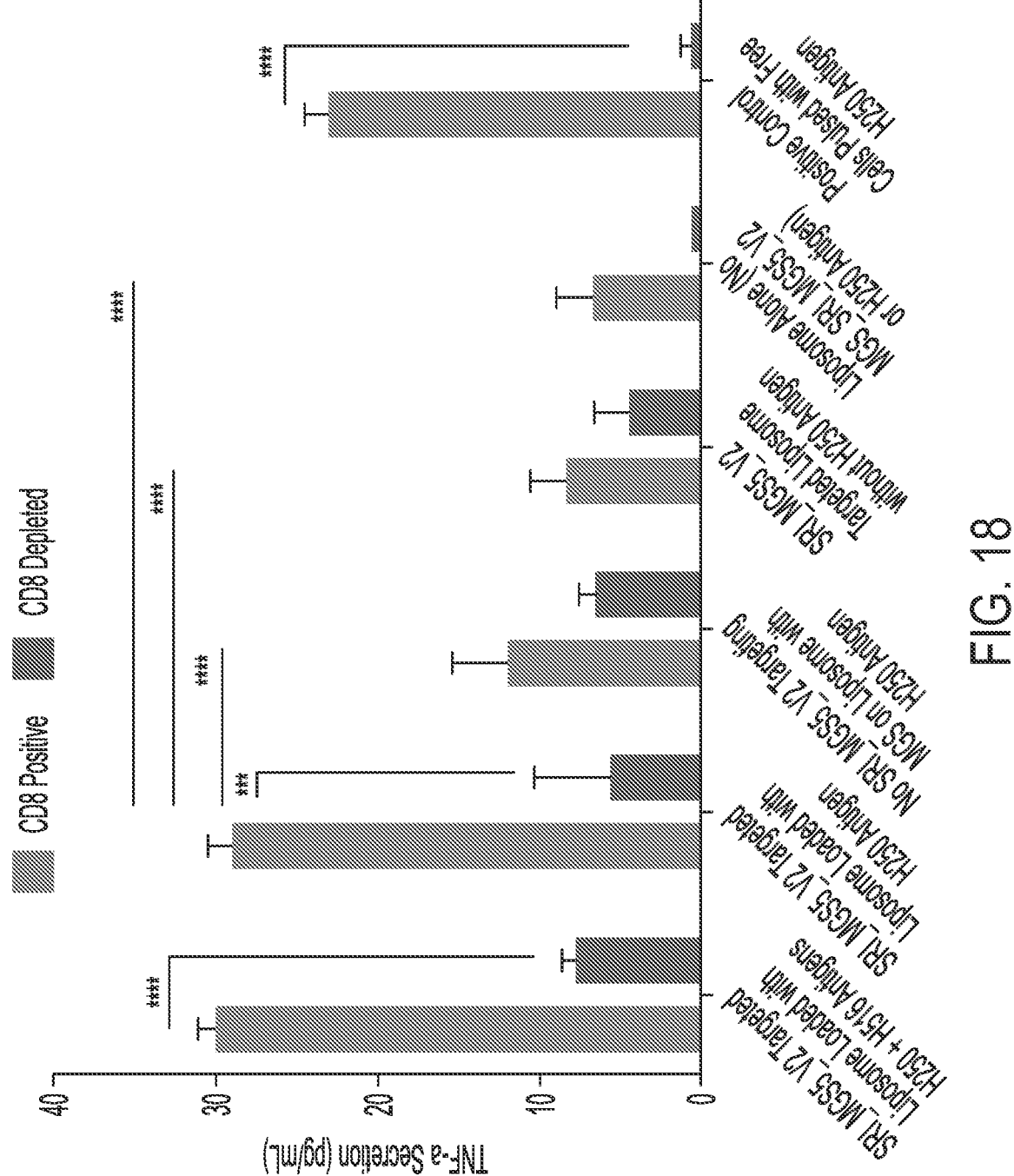
FIG. 18 shows exemplary TNF-α ELISA results indicating that SRI_MGS2_V2 targeting peptide facilitates presentation of encapsulated immunogenic peptide in HLA class I molecules in a murine lung cancer cell line. TALL treated LLC1 cells were co-cultured with HLA-A2 positive PBMCs and culture supernatants were analyzed for TNF-α a secretion. Using a combination of two antigenic peptides (H250 and H516) did not substantially increase the IFN-γ production. When the CD8+ T-cells were depleted from the PBMCs in the assay, the TNF-α production was greatly reduced across all treatment groups. Concentration of all liposomes used in this assay corresponded to ≈4.5 mg/ml of phosphatidyl choline. Free H250 peptide control is incubated at 5 μmol/L.

Co-culture assays were conducted with SRI_MGSS_V2 and the parental peptide to confirm that the optimized peptide mediates delivery and presentation of the antigenic peptide in HLA Class I molecules resulting in comparable antigen presentation and subsequent immune response. The liposomes were loaded with the H250 antigenic peptide and SRI_MGS5_V2 or SRI_MGS5_V1 was conjugated to the external face of the liposome via maleimide chemistry. The liposomes were incubated with H1993 cells followed by co-culture with peripheral blood mononuclear cells (PBMCs) from an anonymous donor that is haplotype HLA A2+ and vaccinated against measles. The ELISA results indicate that both the TALL systems corresponding to the parent SRI_MGS_V1 as well as the SRI_MGS5_V2 showed similar levels of TNF-α production in the co-culture assays (FIG. 16). More experiments testing different liposome variants and assessing TNF-α and INF-γ in co-culture were performed. As shown in FIGS. 17 and 18, the full TALL treatment comprised liposomal encapsulated H250 antigenic peptide and the targeting SRI_MGS5_V2 peptide on the liposomal surface results in both IFN-γ and TNF-α in co-culture experiments. Liposomes that are loaded with H250 peptide but do not contain the targeting peptide or SRI_MGS5_V2 conjugated liposomes with no H250 exhibit a significant decrease in IFN-γ and TNF-α in the same co-culture assay; thus the targeting peptide and the antigenic peptide are both required to observe the delivery and presentation that results in an immune response. Depleting CD8+ T cells from the PBMCs obviates secretion IFN-γ and TNF-α indicating that the immune response is CD8+ dependent. The same experiments were completed using mouse LLC1 cells as the antigen presenting cells and lymph node lymphocytes (LNL) from C57B1/6 mice that had been vaccinated against HA. Similar data is observed indicating that the syngeneic tumor model can be used to assess in vivo response to TALL therapy.

Figure 20:
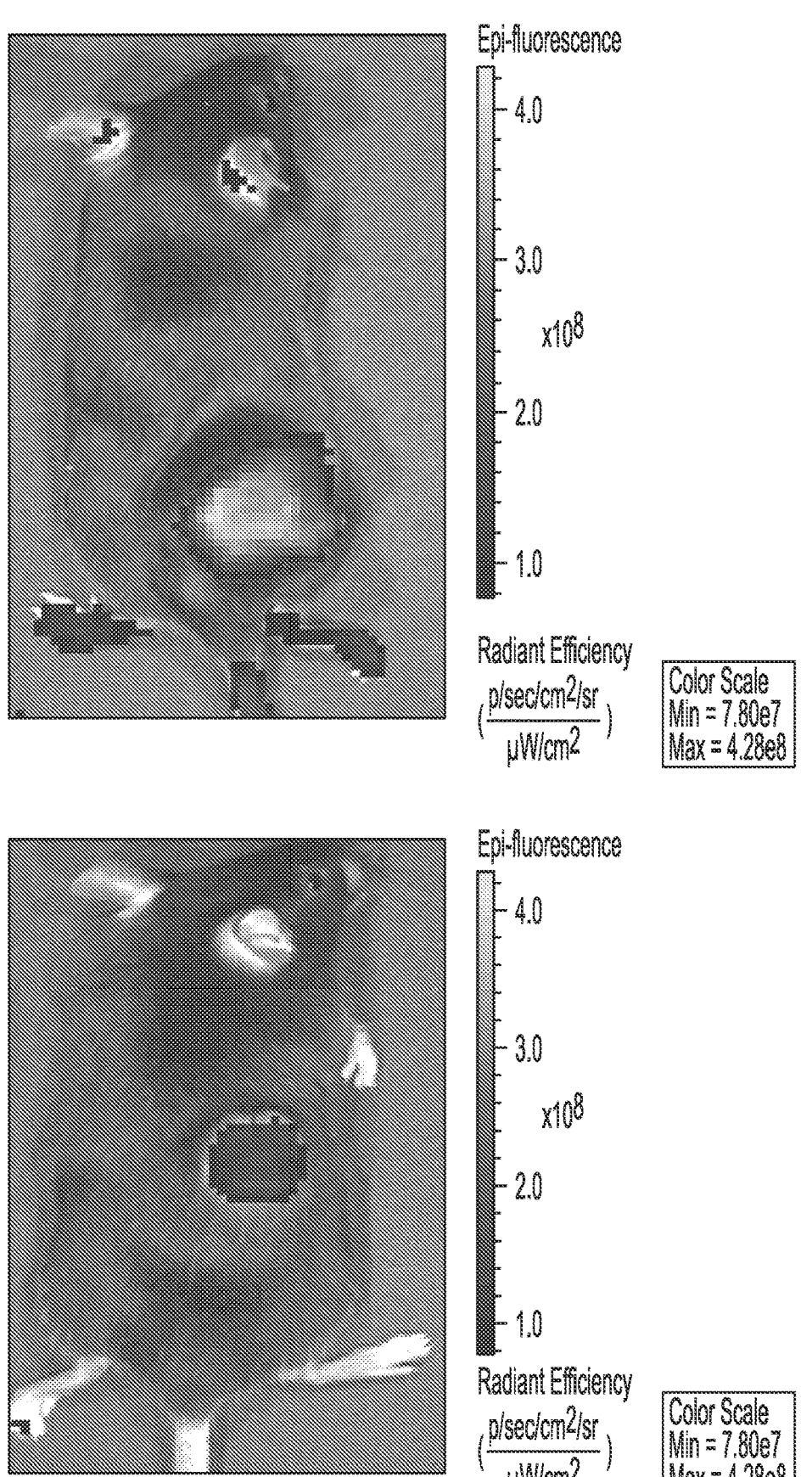
FIG. 20 shows an exemplary in vivo fluorescence image of tumor-bearing C57BL/6 mice 72 hours post injection with either SRI_MGS2_V2 conjugated liposomes (Top) or blank liposomes (Bottom), clearly showing the ability of the targeting peptide to enhance liposome localization within the LLC1 tumors.
Figure 21:
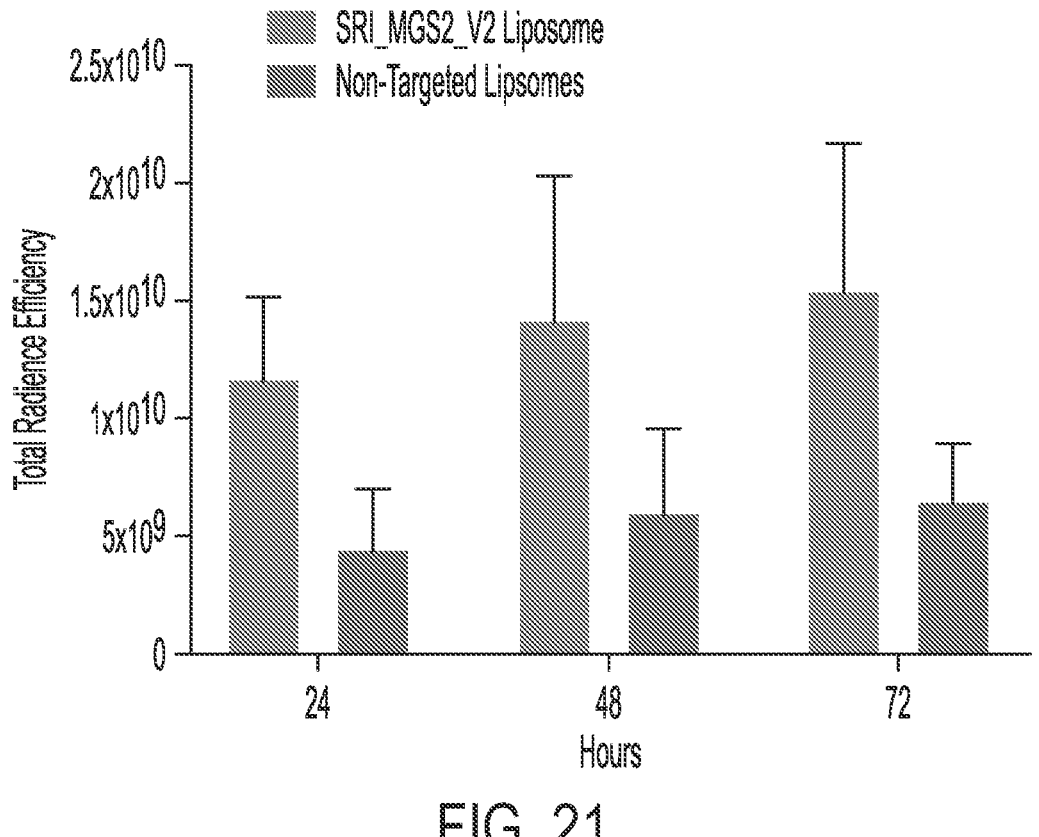
FIG. 21 Shows in vivo quantification of liposome accumulation in the LLC1 tumor in C57BL/6 mice over time.

To test the ability of the SRI_MGS5_V2 can actively direct liposomes to the tumor mass in an animal model, confirm that the targeting peptide can localize the liposomes within the LLC1 tumor mass of C57BL/6 mice. To do this, SRI_MGS2_V2 was conjugated to stealth liposomes that were labeled with the lipophilic NIR dye DiR (1,1'-Dioctadecyl-3,3,3',3'-Tetramethylindotricarbocyanine Iodide) which inserts into the phospholipid membrane of liposomes and enables them to be imaged in vivo. Liposomes not conjugated to the peptide serve as a control. This is especially important as liposomes are known to accumulate in tumor due to the enhance permeability and retention (EPR) effect. Equimolar liposome formulations were injected IV via the tail vein into C57B1/6 mice bearing subcutaneous LLC1 tumors. Tumors were imaged at 24, 48, and 72 H in vivo. As seen in FIG. 20 and FIG. 21 SRI_MGS5_V2-liposomes localized to a much greater extent within the tumor mass when compared to blank liposomes (liposomes containing no targeting peptide). Ex vivo imaging of tumor and the other organs showed a 3-fold greater accumulation of the SRI_MGS5_V2 targeted liposome compared to the non-targeted liposome in the tumor. SRI_MGS5_V2-liposomes showed a 2.5-fold reduction in the lungs compared to non-targeted liposomes. Thus SRI_MGS5_V2 improves tumor targeting while reducing off target accumulation in other organs.

Antigenic peptide optimization was also studied. H250 was utilized as an immunogenic peptide in the TALL system, which is HLA class I restricted and elicits a strong CD8 specific IFNy response in HLA A*02:01 patients. However, a multitude of peptides contribute to the immunogenic response elicited by the pathogen and expanding the repertoire of antigenic peptides delivered by the disclosed delivery system can be useful.

Figure 22:
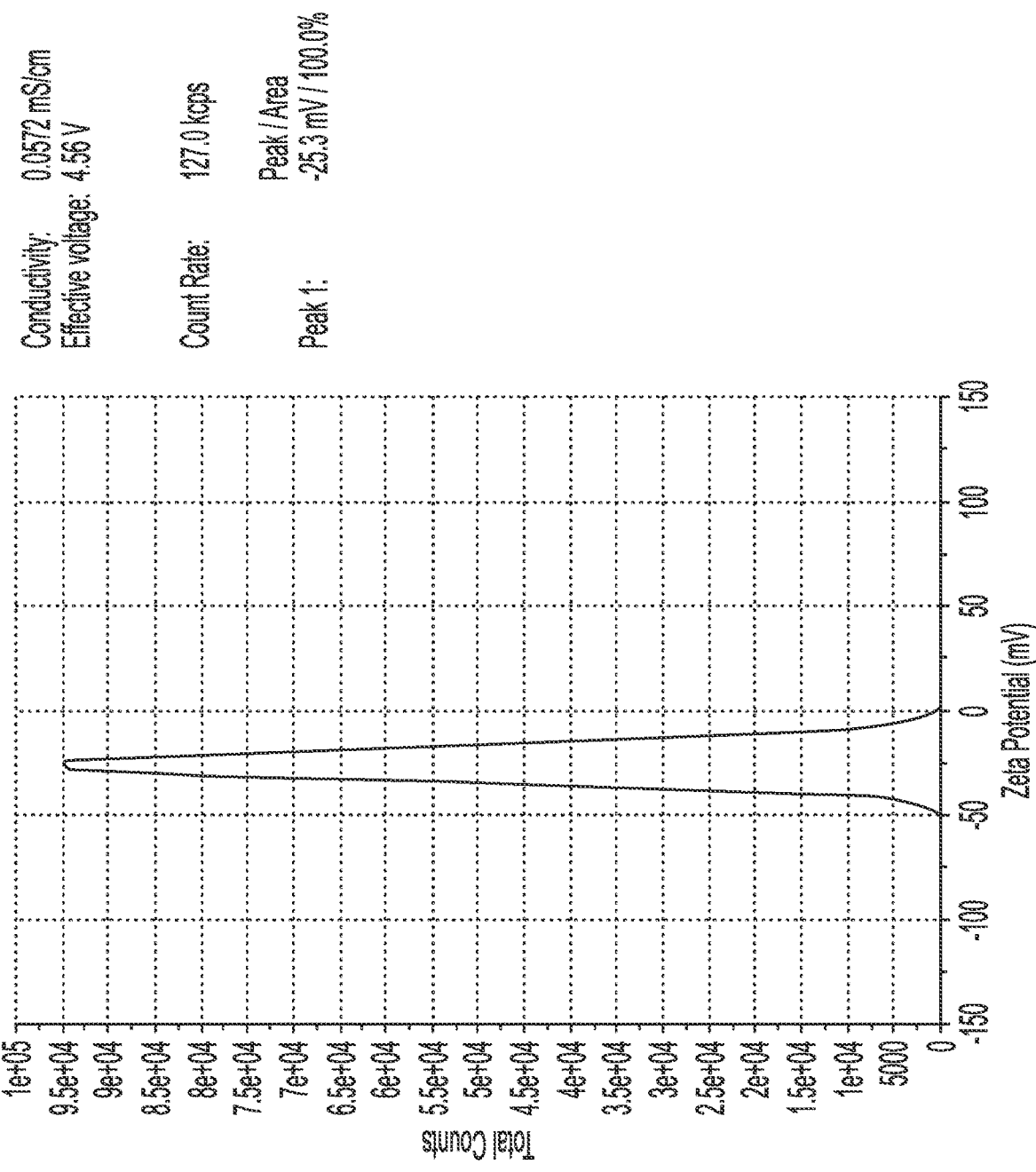
FIG. 22 shows exemplary zeta potential measurement of SRI_MGS5_V2 conjugated liposomes loaded with a equimolar mixture of H250 +H516 antigenic peptides.
Figure 23:
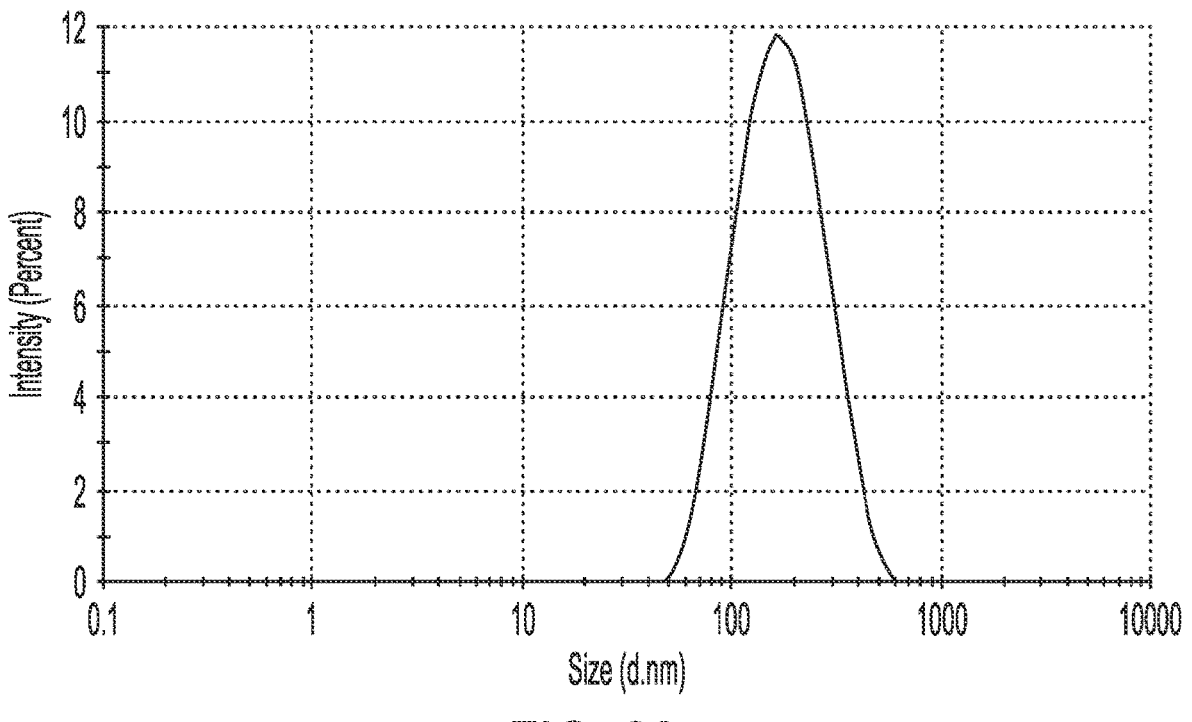
FIG. 23 shows exemplary DLS measurement indicating the size distribution SRI_MGS5_V2 conjugated liposomes containing both the H250 and H516 antigenic peptides.

One objective was to add additional immunogenic peptides to the existing liposome, and test efficacy of the new TALL system via coculture assays. Although initially the measles virus derived H3L and C166 peptides were used as the additional antigenic peptides in the TALL system, they unfortunately proved to be hydrophobic, difficult to purify, and unstable. Therefore, a different antigenic peptide H516 (ILPGQDLQYV) was used to incorporate into the TALL liposomes, which has also been identified from HLA A*02:01 haplotype patients and is highly immunogenic. The dual antigenic peptide (H516+H250) encapsulated liposomes were characterized using DLS and zeta potential measurements (FIGS. 22 and 23). The size of the resulting liposome was determined to be around 155 nm and its zeta potential was determined to be ≈−25.3 mV.

Figure 19:
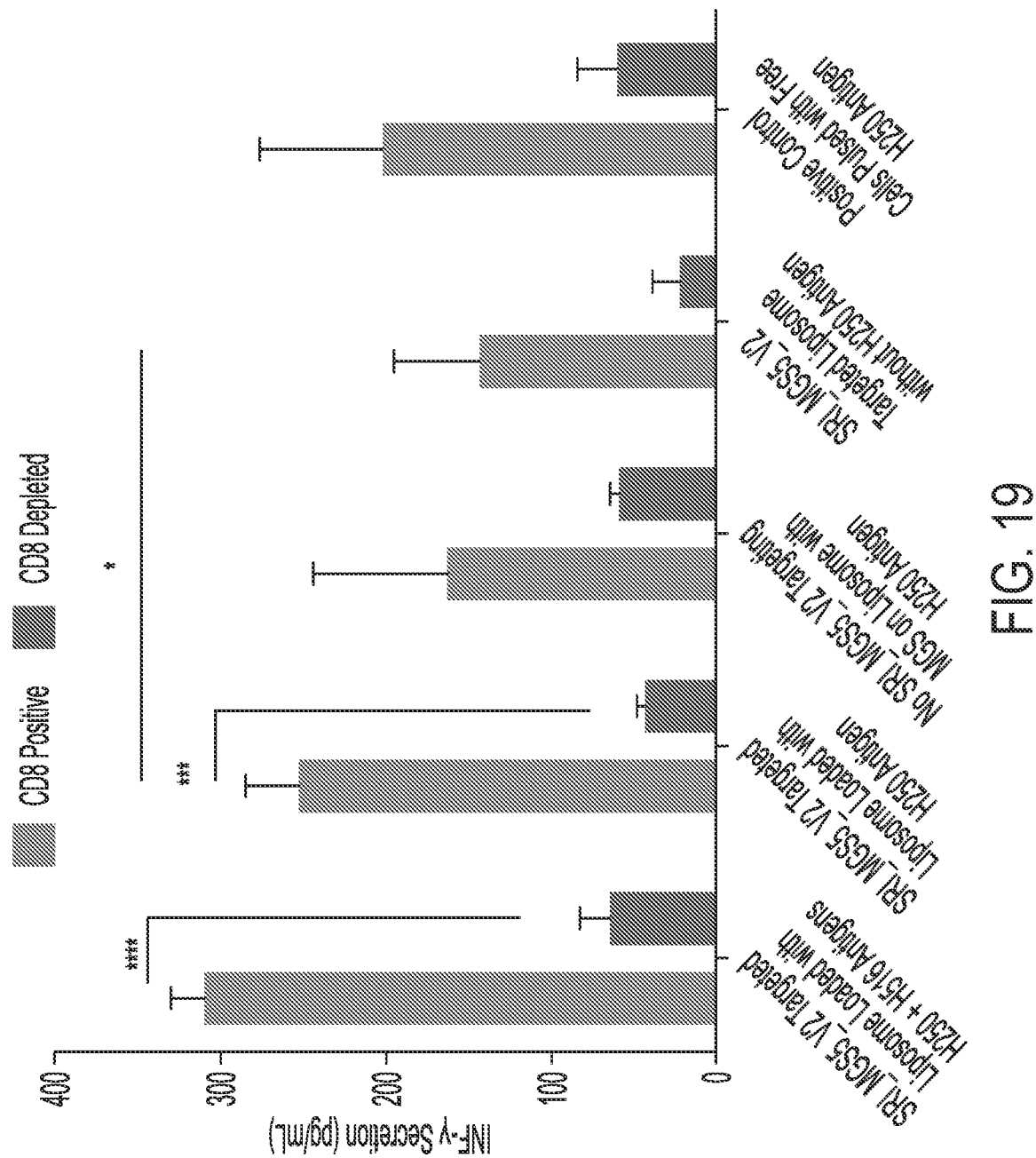
FIG. 19 shows exemplary IFN-γ ELISA results indicating that SRI_MGS2_V2 targeting peptide facilitates presentation of encapsulated immunogenic peptide in HLA class I molecules in a murine lung cancer cell line. TALL treated LLC1 cells were co-cultured with HLA-A2 positive PBMCs and culture supernatants were analyzed for IFN-γ secretion. When the CD8+ T-cells were depleted from the PBMCs in the assay, the IFN-γ production was greatly reduced across all treatment groups. Concentration of all liposomes used in this assay corresponded to ≈4.5 mg/ml of phosphatidyl choline. Free H250 peptide control is incubated at 5 μmol/L.

Co-culture assays were conducted to determine the efficacy of the dual antigen liposomes system compared to the single antigen H250. SRI_MGS5_V2 targeted liposomes containing both H516 and H250 peptides generated the same level of IFNγ and TNF-α secretion as the H250 only liposomes (FIGS. 17-19). In similar fashion, liposomes encapsulating both H250 and C166 antigenic peptides were tested the ability to stimulate TNF-α secretion in a coculture assay. In this case the dual antigenic peptide liposome showed reduced TNF-α compared to liposomes containing either H250 or C166. As the dual antigenic liposomes showed similar or in some cases worse activity, focus was directed on the single H250 antigen. However, the results demonstrate that the system is effective with other antigenic peptides. Given the modular nature of TALL, different antigens can be used based on the patient's needs.

The SRI_MGS5_V2 binds to breast, pancreatic, and glioblastoma cell lines and homes to tumors in syngeneic orthotopic tumor models for each of these tumor types. This indicates that this peptide can have broad utility and recognize many different tumors. As such, it makes sense to focus on the SRI_MGS2_V2 peptide as it has known ability to deliver the antigenic peptide and facilitates presentation of the antigenic peptide in MHC Class 1.

Some experiments required developing luciferase expressing LLC1 cells. In vivo experiments involved generating subcutaneous LLC1 tumors in mice, followed by TALL treatment. In order to generate an orthotopic lung tumor model, it was essential to create a suitable luciferase expressing LLC1 cell line. To obtain stable luciferase expression, lentiviral reporter constructs were utilized. Lentiviral vector constructs containing firefly luciferase genes and transduction of LLC1 cells with them was used to create a stable luciferase expressing LLC1 cell line.

The following procedure was used for generating the pseudoviral vectors used for transduction. The luciferase gene containing plasmid—pTrip-luc was constructed by replacing eGFP sequence of Trip-eGFP plasmid with the firefly luciferase gene between BamHI and XhoI sites. The coding sequence of firefly luciferase was PCR-amplified from the pGL4-Luc vector using the following primers:

```
                                         (SEQ ID NO:12)
5'-AGAGGATCCACCGGTCGCCACCATGGAAGATGC-CAAAAAC-3'
(sense)

(SEQ ID NO:13)
5'-ATAGCTCGAGTTAGACGTT-GATCCTGGCGC-3' (antisense).
```

To produce the pseudoviral particles, $6\times10^5$ Lenti-X 293T cells were seeded 24 hours before transfection in a 6 cm polystyrene dish in 4 ml of DMEM media containing 10% FBS. The next day, cells were transfected using polyethylenimine (PEI, MW 25 Kd) or Lipofectamine 2000 reagent (Invitrogen). The VSV-Gpp pseudoviral particles were packaged by transfecting with 0.5 mL of a DNA mixture comprising of 2 μg of pTrip-Luc, 2 μg CMV-dR8.2 plasmid and 1 μg of HEF-VSV-G plasmid (expressing VSV-G Envelope protein). 16 hours after transfection, the media was replaced. The supernatant containing VSV-Gpp pseudoviral particles was harvested 36-48 hours after transfection and filtered through a 0.45-μm syringe filter.

LLC1 cells were transduced with these pseudoviral vectors for 3-4 hours with the addition of polybrene, following which the vectors were removed and replaced with fresh RPMI media containing 10% FBS. The transduced LLC1 cells were left undisturbed in the incubator for 72 hours. The cells were then counted using a hemocytometer and diluted to obtain a final density of 100 cells in 1 ml of media. 100 μL of this cell suspension was added to each well of a 96-well plate, which results in 80% of the wells containing single cells. These cells were allowed to grow for 7-10 days to obtain a clonal population. Their luciferase expression was tested on a biweekly basis using the Promega Luciferase Assay system for a period of 4 weeks to confirm stable luciferase expression.

Through this process, the luciferase expressing LLC1 cells were found to drift over time and great care must be taken to control for the luciferase expression.

Anti-tumor efficacy of the TALL system was assessed in an orthotopic lung tumor model. Efficacy of the optimized TALL therapy was tested in a syngeneic orthotopic lung cancer model. Testing in immunocompetent C57BL/6 mice can provide a measure of the anti-tumor immune response induced by the TALL therapy in vaccinated animals.

An orthotopic lung tumor model was generated in C57BL/6 mice using luciferase expressing LLC1 cells. C57BL/6 mice were vaccinated using a genetic immunization strategy. A plasmid vector encoding the complete measles hemagglutinin protein containing CMV promotor sequence was developed, which can generate a strong Th1-like CTL response. The plasmid (10 ng) was injected intramuscularly once a week, for a period of four weeks. After the vaccination period, lymphocytes were obtained from the spleen of a vaccinated mouse from the group. Successful vaccination was measured by IFN-γ secretion via coculture assays with TALL treatment and in peptide pulsed lymphocytes. After confirming successful vaccination, $1\times10^6$ Luc-LLC1 cells were delivered into each mouse via tail vein IV injection. Within 2 weeks, bioluminescence was observed in the lungs of the animals upon injection of D-luciferin indicating successful formation of lung tumors.

Figure 24:
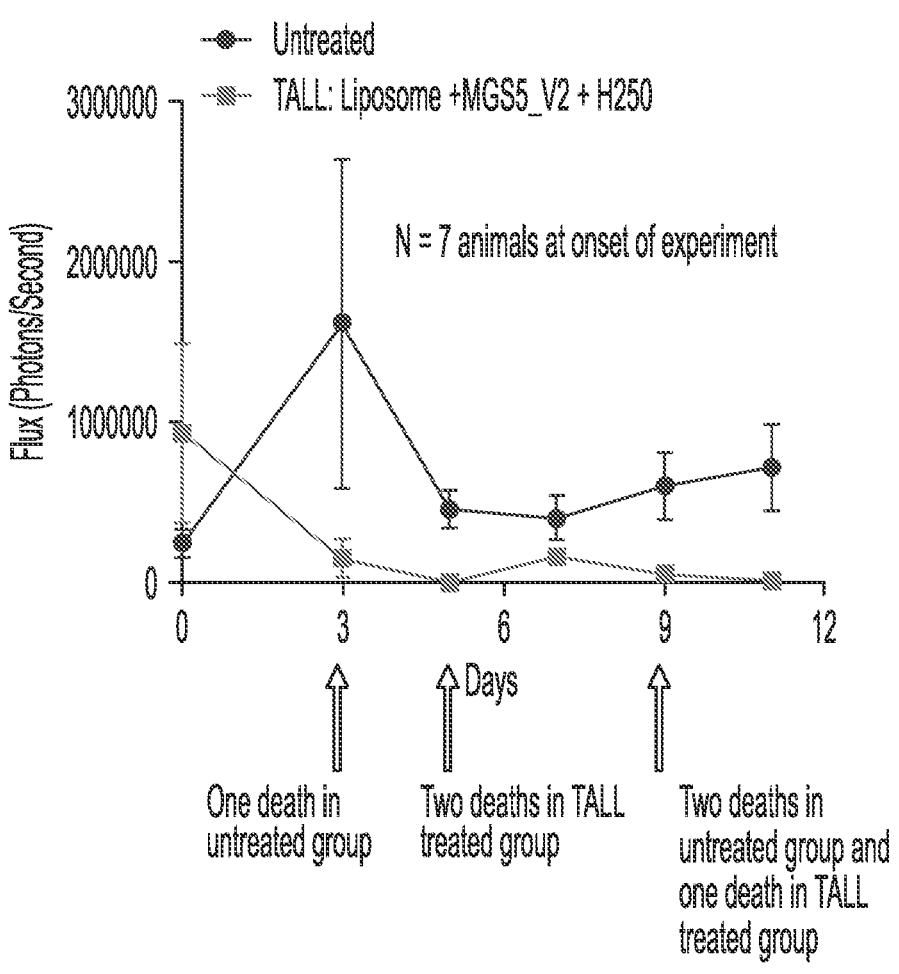
FIG. 24 shows an exemplary average flux (photons/second) emission from the lungs of animals of both TALL treated and untreated groups assessed by IVIS imaging
Figure 25:
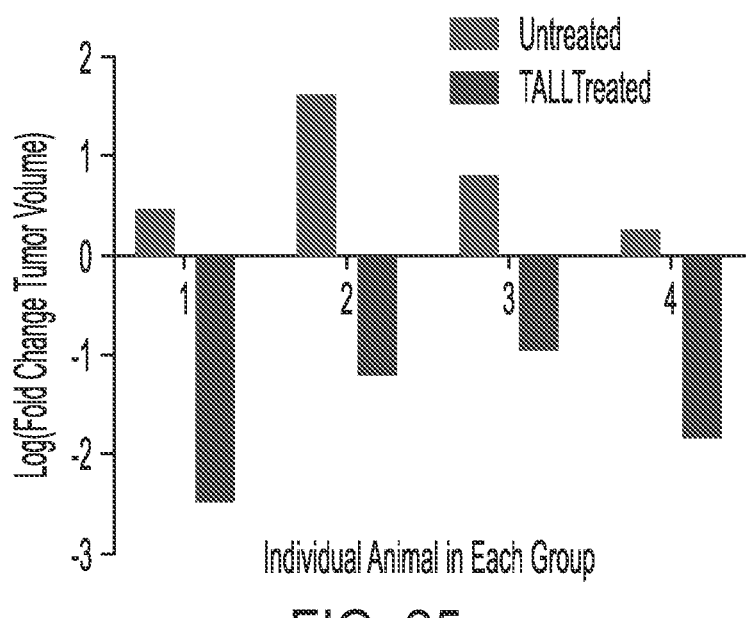
FIG. 25 shows an exemplary change in flux (photons/second) from the lungs from day 0 to day 11 represented as the Log(Flux Day 0/Flux Day 11). Each animal is shown individually. Positive values indicate an increase in tumor size. Negative values represent a decrease in tumor size.

The animals were treated with the TALL targeted liposomes every alternate day for a total of six treatments. A control group contained animals that were not given any treatment. Bioluminescence from the lungs of all mice was measured every alternate day during the entire treatment period via IP injection of 250 μL of 15 mg/mL solution of D-luciferin, followed by IVIS imaging. A reduction in the luciferin expression was observed in the lungs of the animals of the TALL treated group (FIG. 24), which corresponds to a decrease in the tumor size. An increase in luciferase expression was observed in the untreated mice throughout the experiment indicating increasing tumor size. Unfortunately, several animals died in both groups throughout the treatment, as noted in FIG. 24. The change in tumor flux for the surviving animals is shown in FIG. 25. At the end of the experiment, the lungs of the animals were excised, weighed and observed for tumor nodule formations. Lungs of TALL treated animals were found to have fewer or no nodules compared to untreated animals (FIG. 25).

Figure 26:
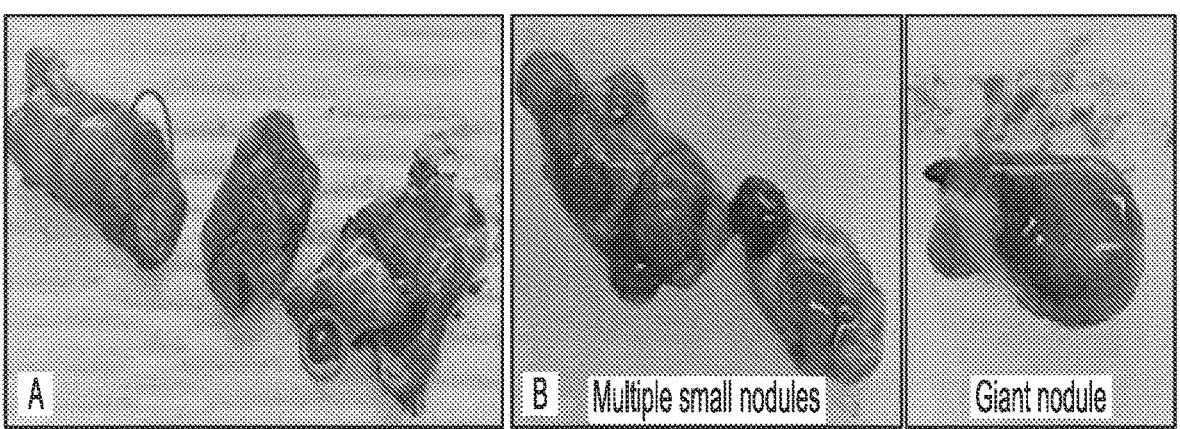
FIG. 26 shows an exemplary assessment of tumor nodule formation in the lungs after TALL treatment. (A) Lungs of the TALL treated group show very few or no nodules (marked in green). (B) Lungs of the untreated animals were found to contain several small or a single large nodule.
Figure 27:
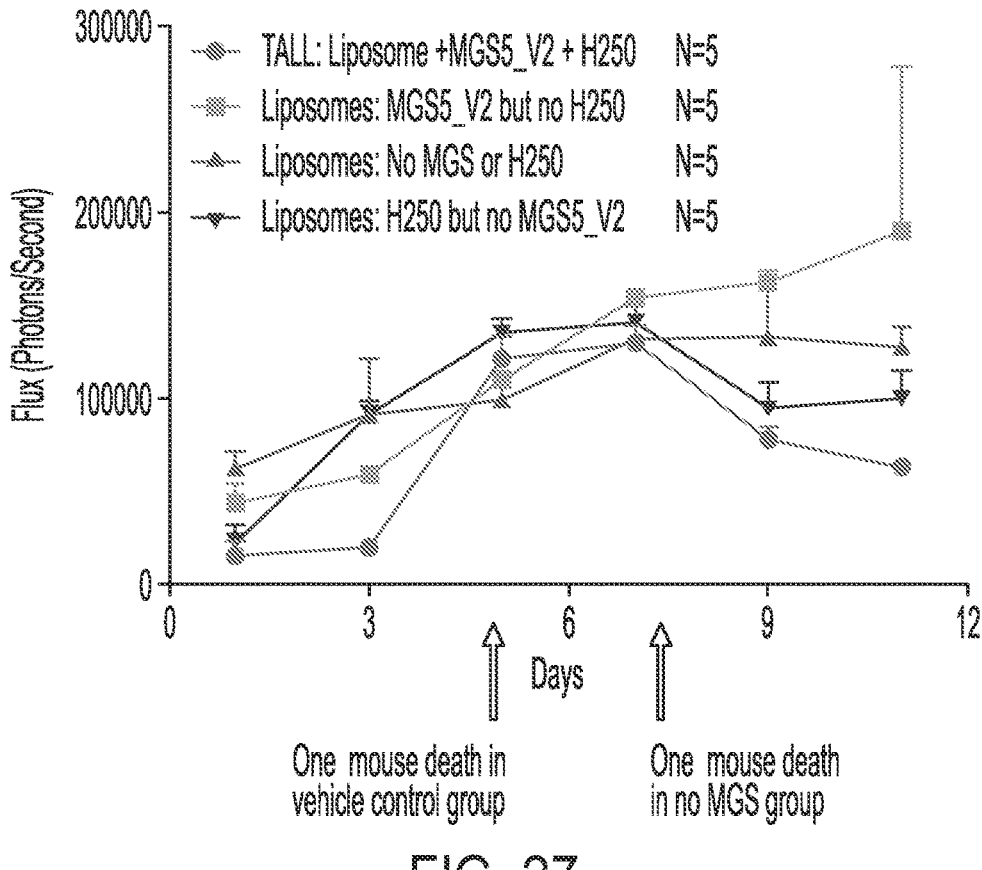
FIG. 27 shows an exemplary average flux (photons/second) emission from the lungs of animals of both TALL treated and untreated groups assessed by IVIS imaging.
Figure 28:
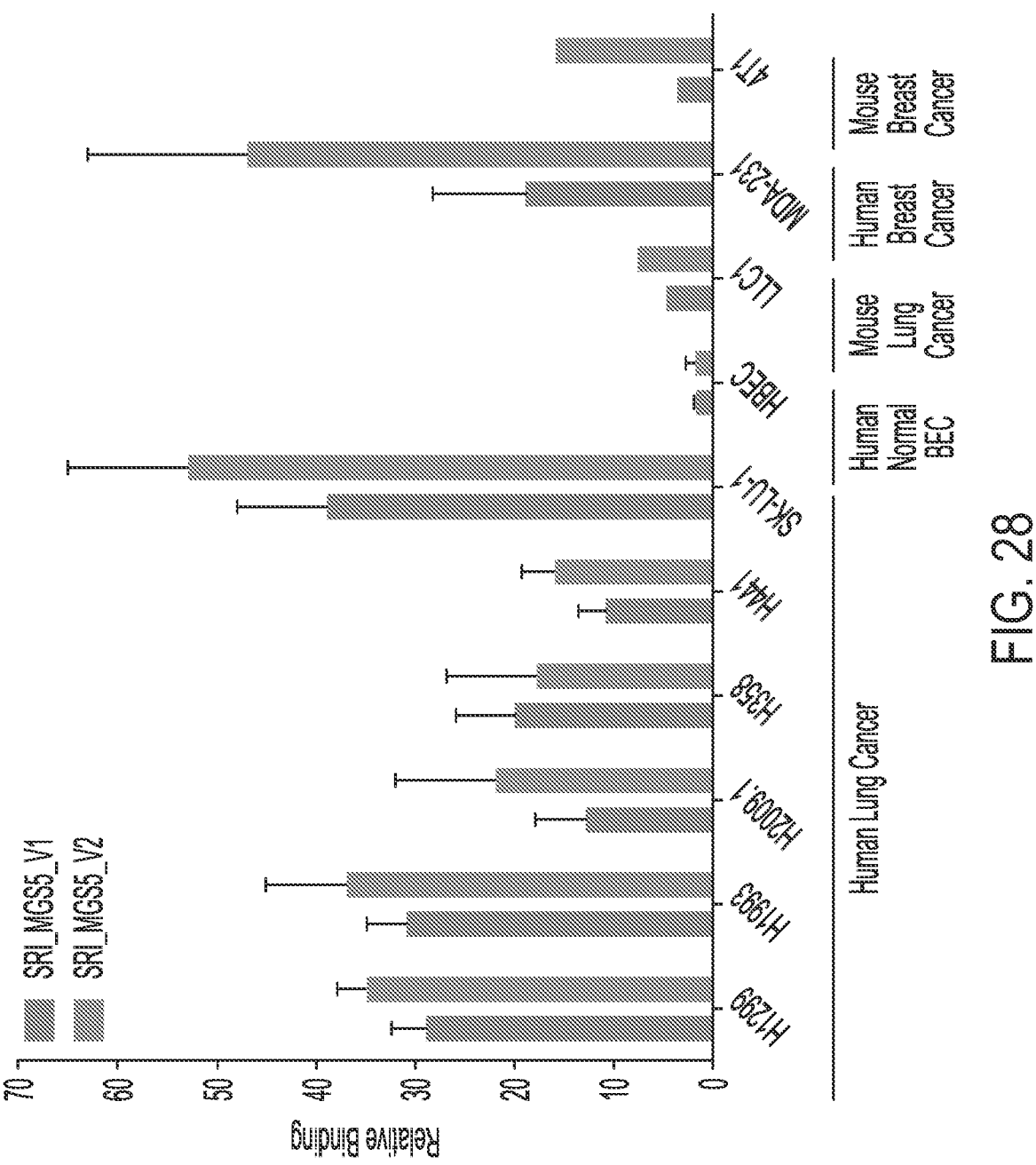
FIG. 28 shows that SRI-MGS5_V2 has improved binding in a panel of cancer cell lines.
Figure 29A:
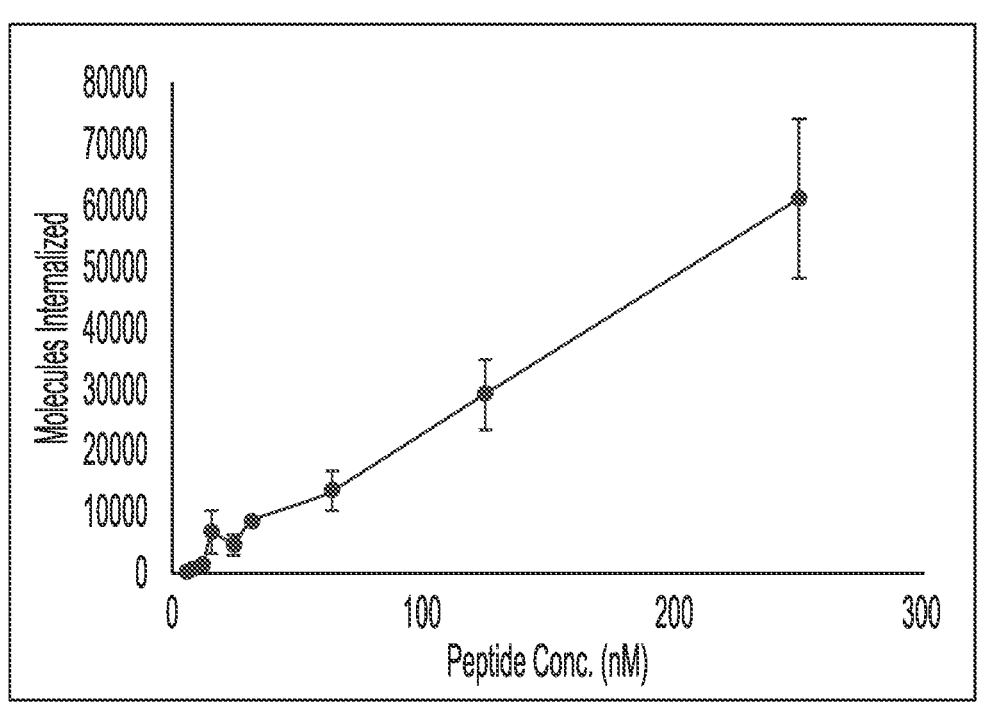
FIG. 29A and 29B show MGS5_V2 Targets an Orthotopic Triple Negative Breast Cancer Tumor in a Syngeneic Mouse Model. A) Quantitative flow cytometry data showing concentration dependent binding and internalization of MGS5_V2 peptide in 4T1 cells. B) TNBC model showing Luc-expressing 4T1 cells implanted in mammary fat pads in a BALB/c mouse (left) and nIR dye-labelled MGS5_V2 peptide targets 4T1 cells and is localized within the tumors (right).
Figure 29B:
Figure 29B:
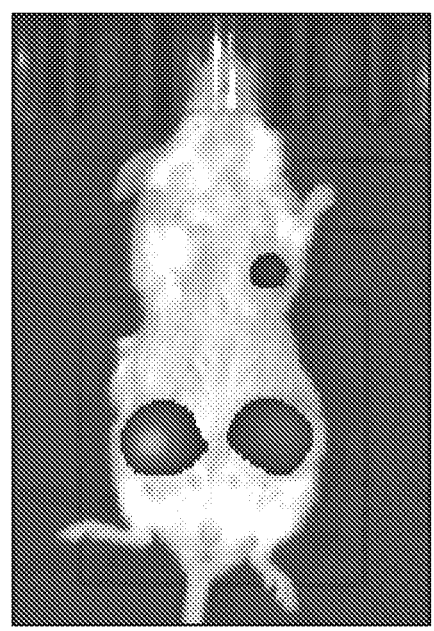
Figure 30A:
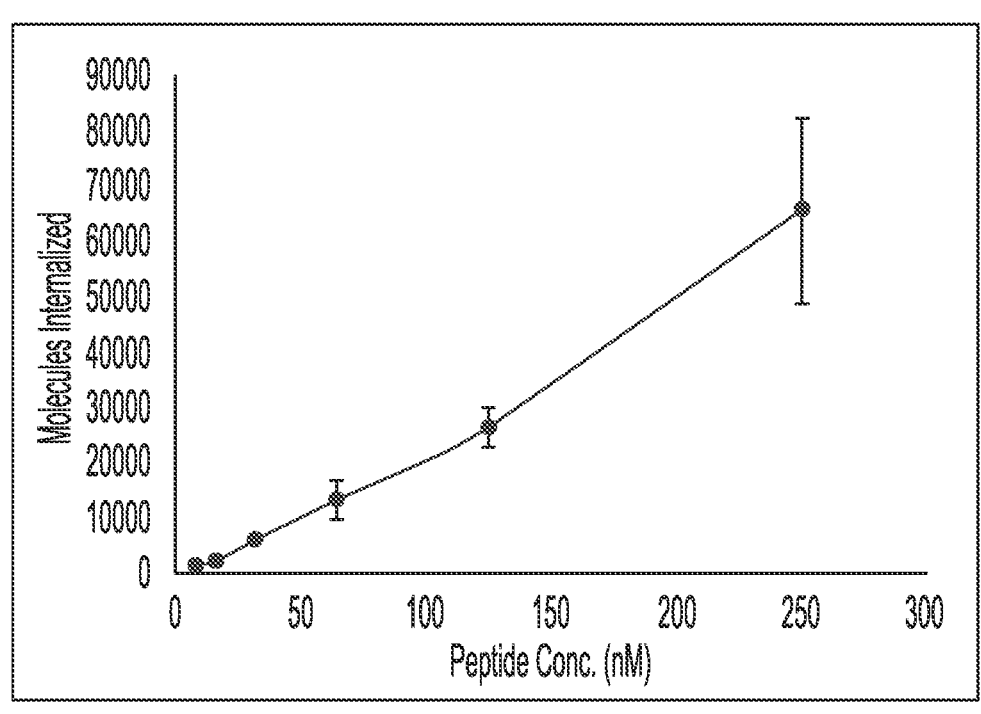
FIGS. 30A and 30B show MGS5_V2 Targets an Orthotopic Pancreatic Ductal Adenocarcinoma Tumor in a Syngeneic Mouse Model. A) Flow cytometry data showing concentration dependent binding and internalization of MGS5_V2 in Pan02 cells. B) PDAC model showing Luc-expressing Pan02 cells implanted in C57BL/6 mouse (left) and Fluorescent dye-labelled MGS5_V2 targets Pan02 cells and is localized in the tumor (right).
Figure 30B:
Figure 30B:
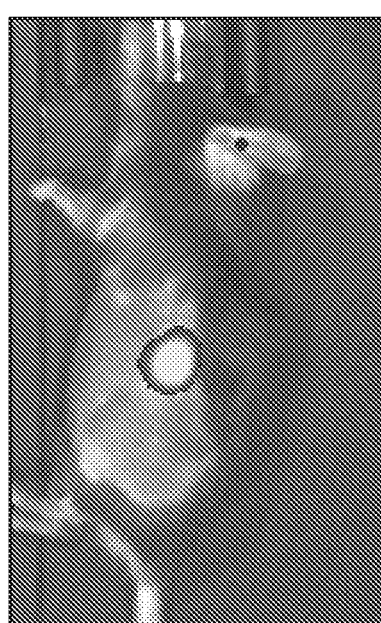
Figure 31A:
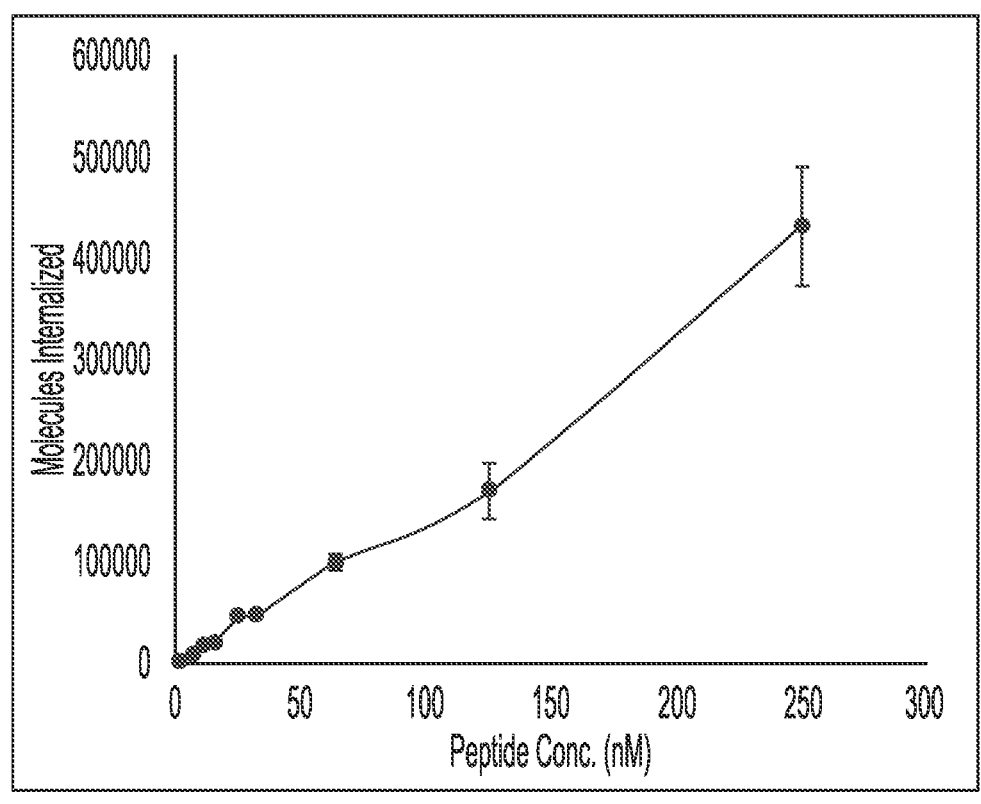
FIGS. 31A and 31B show MGS5_V2 Targets an Orthotopic Glioblastoma Tumor in a Syngeneic Mouse Model. A) Flow cytometry data showing concentration dependent binding and internalization of MGS5_V2 in GL261 cells. B) GBM model showing Luc-expressing GL261 cells implanted in the brain of a B/6 mouse (left) and Fluorescent dye-labelled MGS5_V2 targets GL261 cells (right).
Figure 31B:
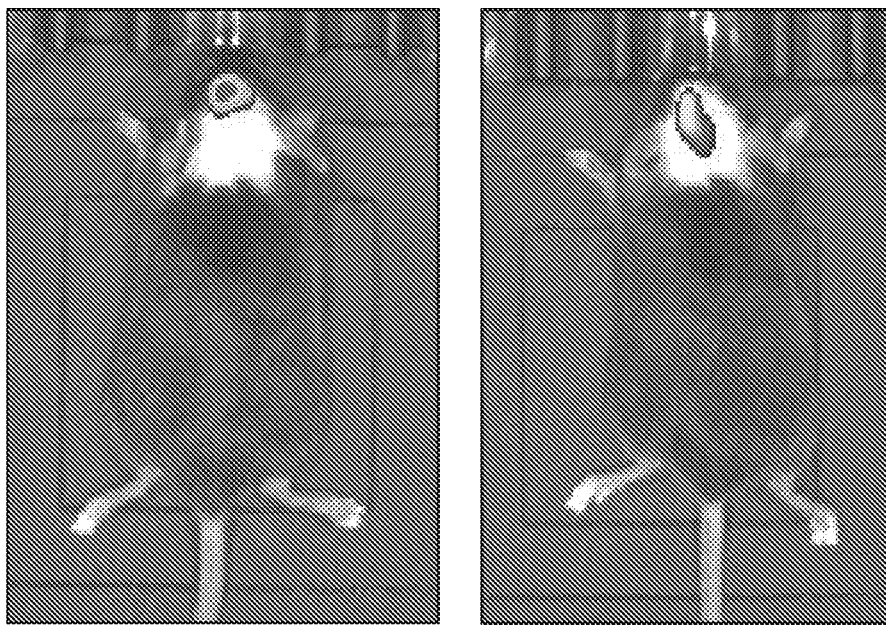
Figure 32:
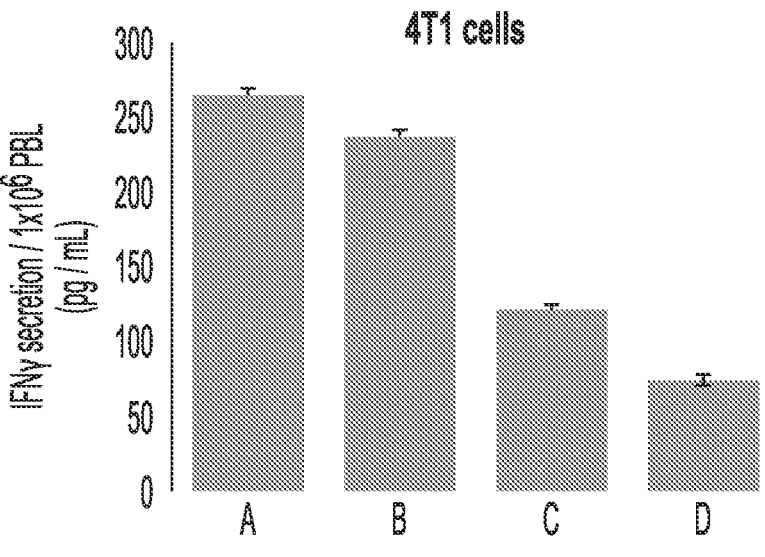
FIG. 32 shows MGS_SRI_MGS5_V2 Mediates Functional Presentation of Antigenic Peptide in Multiple Different Cancer Types. Treatment groups: A—MGS5_V2 Targeted Liposome Loaded with H250 Antigen; B—Positive Control: Cells Pulsed with Free H250 Antigen; C—No MGS on Liposome Loaded with H250 Antigen; D—Blank Liposomes—no H250 Antigen.
Figure 32:
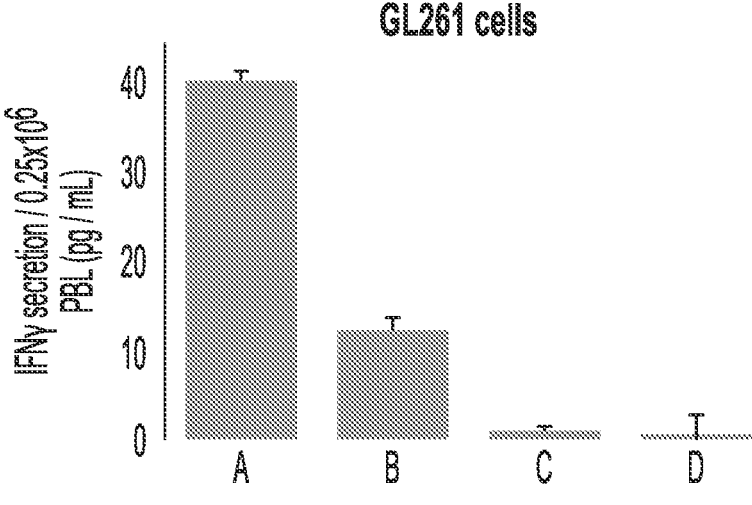
Figure 32:
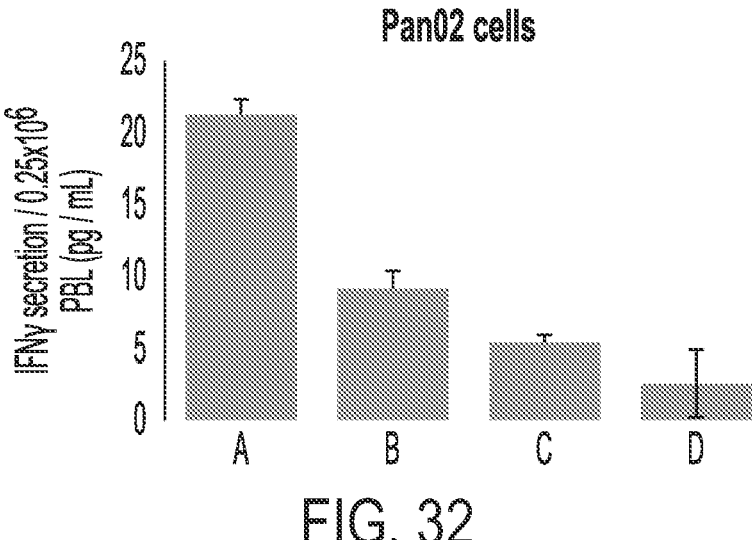
Figure 33:
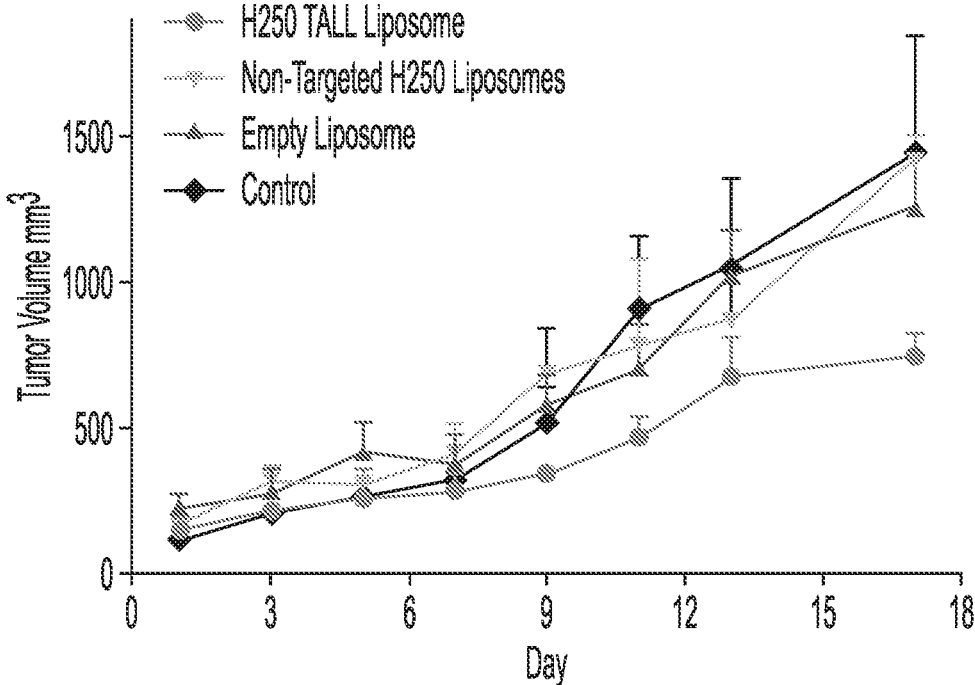
FIG. 33 shows that SRI_MGS_V2 TALL reduces tumor growth in a 4T1 breast cancer model. Mice were treated every other day for 6 doses (2 μg antigenic peptide/mouse).
Figure 33:
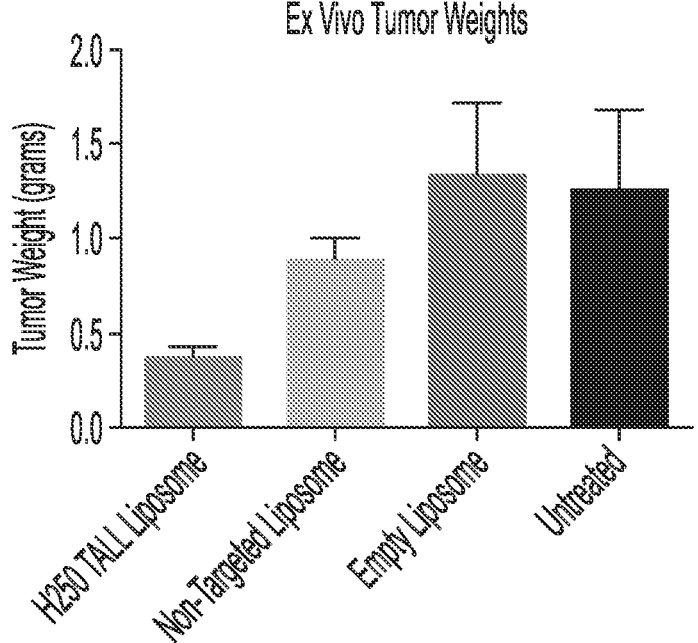

A larger study was conducted with more treatment groups to assess the tumor reduction efficacy of TALL. The treatment groups were as follows: 1) Full TALL liposome treatment; 2) TALL liposomes containing the external targeting peptide, but no antigenic peptide; 3) Blank liposomes containing no targeting or antigenic peptide; 4) TALL liposomes with no targeting peptide. In all four groups, an increase in flux is observed and a reduction in the luciferase expression was observed in the lungs of the animals of the complete TALL treatment group (FIGS. 26 and 27), when compared to all other treatment groups. The decrease in flux emission corresponds to a reduction in total luciferase expression. This indicates a reduction in the total number of tumor cells in the lungs and therefore, a decrease in the tumor size. A smaller decrease in tumor size was observed in the treatment group with no targeting peptide. This is expected as some liposomal accumulation observed in the tumor mass due to the enhanced permeability and retention (EPR) effect with a slow internalization into the cells. An increase in flux emission (and therefore, tumor size) was observed in both the blank liposome treatment group as well as the group treated with no antigenic peptide. This highlights the importance of immunization and presence of the antigenic peptide for the TALL treatment to be successful.

Those skilled in the art will recognize, or be able to ascertain using no more than routine experimentation, many equivalents to the specific embodiments of the method and compositions described herein. Such equivalents are intended to be encompassed by the following claims.

---

We claim:

1. An antigen delivery system comprising a PEGylated liposome, wherein the PEGylated liposome is surface-modified with a cancer-specific cell targeting peptide and comprises an immunogenic human leukocyte antigen (HLA) class I restricted peptide, wherein the HLA class I restricted peptide is a vaccine-dependent, immunogenic HLA class I restricted peptide that is encapsulated by the PEGylated liposome, and wherein the cancer-specific cell targeting peptide comprises a dimer comprising two targeting peptides each consisting of the sequence CH3CO-LQWRRNFGVWARYRL-PEG11 (SEQ ID NO: 1) and which are linked via PEG11 and a lysine branch point to form the sequence CH3CO-LQWRRNFGVWARYRL-PEG11-K-PEG11-LRYRAWVGFNRRWQL-CH3CO (SEQ ID NO: 3) on an external surface of the PEGylated liposome and which is configured to mediate internalization of the PEGylated liposome into a cancer cell and to facilitate presentation of the vaccine-dependent, immunogenic HLA class I restricted peptide, and wherein the antigen delivery system is an immunotherapeutic.

2. The antigen delivery system of claim 1, wherein the vaccine-dependent, immunogenic HLA class I restricted peptide is measles virus hemagglutinin peptide H250.

3. The antigen delivery system of claim 1, wherein the vaccine-dependent, immunogenic HLA class I restricted peptide is influenza virus hemagglutinin peptide HA.

4. The antigen delivery system of claim 1, wherein the vaccine- dependent, immunogenic HLA class I restricted peptide is smallpox virus H-2Kd-restricted vaccinia-specific peptide, A5275-83, which is VACV-A52.

5. The antigen delivery system of claim 1, wherein the vaccine-dependent, immunogenic HLA class I restricted peptide is selected from the group consisting of:

H250, which is SMYRVFEVGV (SEQ ID NO: 5);

C166, which is SLWGSLLML (SEQ ID NO: 6);

H38, which is LLAVIFVMFL (SEQ ID NO: 7);

H516, which is ILPGQDLQYV (SEQ ID NO: 8);

H3L, which is SLSAYIIRV (SEQ ID NO: 9);

E2L, which is KIDYYIPYV (SEQ ID NO: 10); and 01L, which is GLNDYLHSV (SEQ ID NO: 11).

6. The antigen delivery system of claim 1, wherein the antigen delivery system does not comprise any viral particles, toxins, or biologically-derived material.

7. The antigen delivery system of claim 1, wherein the cancer-specific cell targeting peptide is acetylated on the N-terminus.

8. The antigen delivery system of claim 1, wherein the cancer-specific cell targeting peptide comprises a PEG linker on the C-terminus.

9. The antigen delivery system of claim 1, wherein the dimer further comprises a conjugation moiety on the C-terminal side of the lysine branch point, wherein the conjugation moiety allows for conjugation to the liposome.

\* \* \* \* \*